United States Patent [19]

Niemeyer et al.

[11] Patent Number: 6,140,551
[45] Date of Patent: Oct. 31, 2000

[54] ABSORBENT ARTICLE WITH VISUALLY AND TACTILELY DISTINCTIVE OUTER COVER

[75] Inventors: Jean Feyen Niemeyer, Appleton; Thomas Allan Eby, Greenville; David Willis Heyn; Allen Todd Leak, both of Neenah, all of Wis.; Jeffrey Lawrence McManus, Canton; Steven Walter Moster, Atlanta, both of Ga.; Dale Arthur Peterson, Neenah, Wis.; Alan Francis Schleinz, Appleton, Wis.; Gordon Allen Shaw; Michael Donald Sperl, both of Greenville, Wis.; Gregory Todd Sudduth, Cumming, Ga.; Paula Kay Zoromski, Appleton, Wis.

[73] Assignee: Kimberly-Clark Worldwide, Inc., Neenah, Wis.

[21] Appl. No.: 09/067,803

[22] Filed: Apr. 29, 1998

Related U.S. Application Data

[63] Continuation-in-part of application No. 09/035,246, Mar. 5, 1998, abandoned.
[60] Provisional application No. 60/074,538, Feb. 12, 1998, and provisional application No. 60/060,365, Sep. 29, 1997.

[51] Int. Cl.[7] .............................. A61F 13/15; A61F 13/20
[52] U.S. Cl. ........................ 604/367; 604/358; 604/365; 604/378; 604/380; 604/383; 604/384; 604/385.01
[58] Field of Search ................................... 604/358, 365, 604/367, 373, 374, 384, 385.1, 383, 378, 380, 385.01

[56] References Cited

U.S. PATENT DOCUMENTS 3,675,654 7/1972 Baker et al. .
3,794,024 2/1974 Kokx et al. .
3,901,236 8/1975 Assarsson et al. .

(List continued on next page.)

FOREIGN PATENT DOCUMENTS

| 0 148 115 A1 | 7/1985 | European Pat. Off. . |
| 0 217 032 A2 | 4/1987 | European Pat. Off. ....... D04H 13/00 |
| 0 452 727 B1 | 10/1991 | European Pat. Off. ....... D04H 13/00 |
| 0 604 731 A1 | 7/1994 | European Pat. Off. ........ B32B 31/00 |
| 0 738 505 A1 | 10/1996 | European Pat. Off. . |
| 0 776 645 A1 | 6/1997 | European Pat. Off. . |
| 43 11 867 A1 | 10/1994 | Germany . |
| WO 95/16562 A1 | 6/1995 | WIPO .............................. B32B 5/24 |
| WO 97/48358 A1 | 12/1997 | WIPO . |

OTHER PUBLICATIONS

Derwent World Patent Database abstract of EP 148115: Description of R. Levy, "Baby's Napkin With Urine Indicator."

(List continued on next page.)

Primary Examiner—John G. Weiss
Assistant Examiner—Miley Craig Peppers, III
Attorney, Agent, or Firm—Paul Yee

[57] ABSTRACT

An absorbent article, such as the shown diaper (10), has a front waistband portion (14), a back waistband portion (12) and an intermediate portion (16) interconnecting said front and back waistband portions. The article includes a backsheet member (30), a liquid permeable topsheet layer (28), and an absorbent body (32) sandwiched between the topsheet layer (28) and backsheet member (30). The backsheet member includes an air permeable, polymer sheet layer (96), and a first, outward nonwoven fibrous web (94) attached to or otherwise operatively joined with a major facing surface (78) of the polymer sheet layer (96) at a plurality of individual, spaced apart thermal bonds (98). The outward nonwoven web (94) includes a plurality of fibers having substantially unbonded lengths which extend substantially continuously between at least an adjacent pair of the bonds, and the substantially unbonded fiber lengths are arched away from an outward surface of the thermal bonds by arch heights (60) which provides a distinctive embossing element depth value. In addition, the fibers of the outward nonwoven web can have a selected denier, and the outward nonwoven web (94) can have a selected basis weight.

20 Claims, 9 Drawing Sheets

U.S. PATENT DOCUMENTS

| | | |
|---|---|---|
| 4,022,211 | 5/1977 | Timmons et al. . |
| 4,076,663 | 2/1978 | Masuda et al. . |
| 4,192,311 | 3/1980 | Felfoldi . |
| 4,231,370 | 11/1980 | Mroz et al. . |
| 4,286,082 | 8/1981 | Tsubakimoto et al. . |
| 4,333,979 | 6/1982 | Sciaraffa et al. . |
| 4,663,220 | 5/1987 | Wisneski et al. . |
| 4,699,823 | 10/1987 | Kellenberger et al. . |
| 4,704,116 | 11/1987 | Enloe . |
| 4,705,513 | 11/1987 | Sheldon et al. . |
| 4,725,473 | 2/1988 | Van Gompel et al. . |
| 4,741,941 | 5/1988 | Englebert et al. . |
| 4,753,646 | 6/1988 | Enloe . |
| 4,818,600 | 4/1989 | Braun et al. ............................ 428/290 |
| 4,867,150 | 9/1989 | Gilbert .................................... 128/155 |
| 4,916,005 | 4/1990 | Lippert et al. . |
| 4,938,753 | 7/1990 | Van Gompel et al. . |
| 5,019,073 | 5/1991 | Roessler et al. . |
| 5,032,122 | 7/1991 | Noel et al. . |
| 5,078,708 | 1/1992 | Haque . |
| 5,226,992 | 7/1993 | Morman . |
| 5,399,219 | 3/1995 | Roessler et al. . |
| 5,486,166 | 1/1996 | Bishop et al. . |
| 5,490,846 | 2/1996 | Ellis et al. . |
| 5,540,796 | 7/1996 | Fries . |
| 5,562,650 | 10/1996 | Everett et al. . |
| 5,575,785 | 11/1996 | Gryskiewicz ........................ 604/385.2 |
| 5,595,618 | 1/1997 | Fries et al. . |
| 5,599,420 | 2/1997 | Yeo et al. . |
| 5,605,735 | 2/1997 | Zehner et al. . |
| 5,615,460 | 4/1997 | Weirich et al. . |
| 5,624,429 | 4/1997 | Long et al. . |
| 5,690,624 | 11/1997 | Sasaki et al. . |
| 5,695,868 | 12/1997 | McCormack . |
| 5,897,541 | 4/1999 | Uitenbroek et al. . |

OTHER PUBLICATIONS

Derwent World Patent Database abstract of DE 4,311,867: Description of H. Boich et al., "Impermeable Fibre Film Composite Esp. For Nappies."

Patent Cooperation Treaty Search Report from the International Search Authority, International Application No. PCT/US 98/20342 dated Jan. 21, 1999.

American Society for Testing Materials (ASTM) Designation: E 96–80, "Standard Test Methods for Water Vapor Transmission of Materials," pp. 742–751, published Feb. 1981.

Federal Test Method Standard (FTMS) No. 191A, Method 5514, "Water Resistance of Cloth; Low Range, Hydrostatic Pressure Method," Jul. 20, 1978, 3 pages.

American Society for Testing Materials (ASTM) Designation: D 737–96, "Standard Test Method for Air Permeability of Textile Fabrics," pp. 236–240, published Apr. 1996.

American Society for Testing Materials (ASTM) Designation: D 1117–80, "Standard Test Methods of Testing Nonwoven Fabrics," pp. 240–246, published May 1980.

American Society for Testing Materials (ASTM) Designation: D 1117–97, "Standard Test Methods for Nonwoven Fabrics," pp. 311–313, published Jun. 1997.

American Society for Testing Materials (ASTM) Designation: D 1682–64 (Reapproved 1975), "Standard Test Methods for Breaking Load and Elongation of Textile Fabrics," pp. 454–459, published Oct. 1964.

American Society for Testing Materials (ASTM) Designation: D 2244–85, "Standard Test Method for Calculation Of Color Differences From Instrumentally Measured Color Coordinates," pp. 388–393, published Jan. 1986.

American Society for Testing Materials (ASTM) Designation: D 5034–95, "Standard Test Method For Breaking Strength And Elongation Of Textile Fabrics (Grab Test)," pp. 674–681, published Jul. 1995.

American Society for Testing Materials (ASTM) Designation: D 5035–90, "Standard Test Method For Breaking Force and Elongation of Textile Fabrics (Strip Force)," pp. 726–731, published May 1990.

American Society for Testing Materials (ASTM) Designation: D 5035–95, "Standard Test Method For Breaking Force and Elongation of Textile Fabrics (Strip Method)," pp. 682–688, published Jul. 1995.

American Society for Testing Materials (ASTM) Designation: D 5169–91, "Standard Test Method for Shear Strength (Dynamic Method) of Hook and Loop Touch Fasteners," pp. 687–689, published Nov. 1991.

American Society for Testing Materials (ASTM) Designation: D 5170–91, "Standard Test Method for Peel Strength ("T" Method) of Hook and Loop Touch Fasteners," pp. 690–692, published Nov. 1991.

American Society for Testing Materials (ASTM) Designation: E 308–85, "Standard Method for Computing the Colors of Objects by Using the CIE System," pp. 181–207, published Apr. 1985.

American Society for Testing Materials (ASTM) Designation: E 313–73, "Standard Test Method for Indexes of Whiteness and Yellowness of Near–White, Opaque Materials," pp. 771–774, published Jan. 1974.

CIE Publication No. 15.2, *Colorimetry*, Second Edition, 1986, pp. 1–74.

Federal Test Method Standard (FTMS) No. 191A, Method 5306, "Abrasion Resistance of Cloth; Rotary Platform, Double–Head (Taber) Method," Jul. 20, 1978, 7 pages.

TAPPI Official Test Method T 543 om–94, "Bending Resistance of Paper (Gurley Type Tester)," published by the TAPPI Press, Atlanta, Georgia, pp. 1–5.

ABSORBENT ARTICLE WITH VISUALLY AND TACTILELY DISTINCTIVE OUTER COVER

This application is a continuation-in-part of U.S. application Ser. No. 09/035,246 filed on Mar. 5, 1998 now abandon, which claims the benefit of Provisional Application No. 60/074,538 filed on Feb. 12, 1998, and Provisional Application No. 60/060,365 filed on Sep. 29, 1997.

FIELD OF THE INVENTION

The present invention relates to garment articles. More particularly, the present invention relates to absorbent articles, desirably disposable absorbent articles, which have an outercover distinctively configured to provide improved visual and tactile benefits.

BACKGROUND OF THE INVENTION

Conventional garment articles, such as disposable diapers and other disposable absorbent articles, have typically employed adhesive or mechanical fasteners which attach appointed waistband sections of the articles around a wearer. In addition, various configurations of waist elastics, leg elastics, elasticized liners, and elasticized outercovers have been employed on garment articles to help produce and maintain the fit of the articles about the body contours of the wearer.

The external surfaces of such disposable absorbent products may include a nonwoven fibrous material or a matte-finished film material. In some arrangements, pattern embossments have been formed into the outer surface of the outer cover to provide a decorative pattern.

It has been proposed to subject a bonded web of continuous thermoplastic polypropylene filaments to hot embossing in a gross pattern, thereby producing a permanent web deformation and increasing the effective web thickness.

It has also been proposed to selectively point-bond or pattern-bond a non-stretched lofty nonwoven fibrous material to a stretched elastomeric film, then allowing the film to retract, thereby gathering the fibrous material in the direction of the elastomer film retraction. This causes the fibrous material to arch up away from the elastomer film, thereby producing fibrous pile or arched filament height between the selective bond points. This method, however, generally requires a comparatively expensive, sophisticated elastomeric film laminae, the inclusion of which may not be desirable within the finished outer cover laminate design.

It has also been proposed to freeze thermoplastic filaments onto a three dimensional forming wire in order to produce a low density, high loft finished web. Such a method has employed a curtain of molten meltblown polypropylene that is deposited onto a three-dimensional forming wire. The very fine filament diameters and relatively short individual filament lengths of the meltblown fibers provide an integrated filamentary mat onto the forming wire that provides suitable three dimensional stability in the formed web after it is removed from the forming wire.

Conventional garment articles, such as those described above, have not provided desired levels of durability, low cost, aesthetic appeal and tactile properties. As a result, there has been a continued need for garments having improvements in such properties.

BRIEF DESCRIPTION OF THE INVENTION

Generally stated, the present invention provides an absorbent article having a front waistband portion, a back waistband portion and an intermediate portion. The article includes a flexible and readily conformable backsheet member, a liquid permeable topsheet layer, and an absorbent body sandwiched between the backsheet member and the topsheet layer. The backsheet member includes an air permeable, polymer sheet layer, and a first, outward nonwoven fibrous web attached to a major facing surface of the polymer sheet layer at a plurality of individual, spaced apart thermal bonds. The outward nonwoven web includes a plurality of fibers having substantially unbonded lengths which extend between at least an adjacent pair of the bonds, and the substantially unbonded fiber lengths are lofted away from an outward surface of the thermal bonds to provide a distinctive embossing element depth value. In addition, the fibers of the outward nonwoven web can have a selected denier, and the outward nonwoven web can have a selected basis weight.

In desired arrangements, the air permeable polymer sheet layer can, for example, have a WVTR value of at least a minimum of about 500 g/m$^2$ per 24 hr, and the arch heights of the unbonded fiber lengths and the thermal bonds can provide an embossing element depth value of at least about 175 µm. In other desired configurations, the fibers of the outward nonwoven web may have a denier of not more than a maximum of about 3 dpf, and the outward nonwoven web may have a basis weight of not more than about 55 g/m$^2$.

By incorporating its various aspects, the article of present invention can provide an article having a visually and tactilely distinctive laminate outer cover. The outer cover has a lofty outward surface and can be produced at low cost. A distinctive combination of gross embossments and a selected fibrous nonwoven outermost laminate layer can provide a preferred, aesthetically pleasing outer cover having improved appearance, abrasion resistance and feel, which can more effectively connote apparel-like qualities. A selected configuration of a gross bonding or embossment pattern, and particular amounts of loft in the nonwoven fabric have been found to be important parameters for providing a preferred, three-dimensionality in a surface of an economical, low density, fibrous nonwoven outer cover. Accordingly, the various aspects of the present invention can advantageously provide a distinctive article having a low basis weight outer cover with improved durability, bulk and softness.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The various aspects and embodiments of the invention will be described in the context of a disposable absorbent article, such as a disposable diaper. It is, however, readily apparent that the present invention could also be employed with other articles, such as caps, gowns, shoe covers, feminine care articles, children's training pants, incontinence garments and the like. Typically, the disposable articles are intended for limited use and are not intended to be laundered or otherwise cleaned for reuse. A disposable diaper, for example, is discarded after it has become soiled by the wearer. Optionally, a disposable diaper may include a single-use, absorbent insert, and a limited-use outer cover which may be reused several times.

Figure 1:
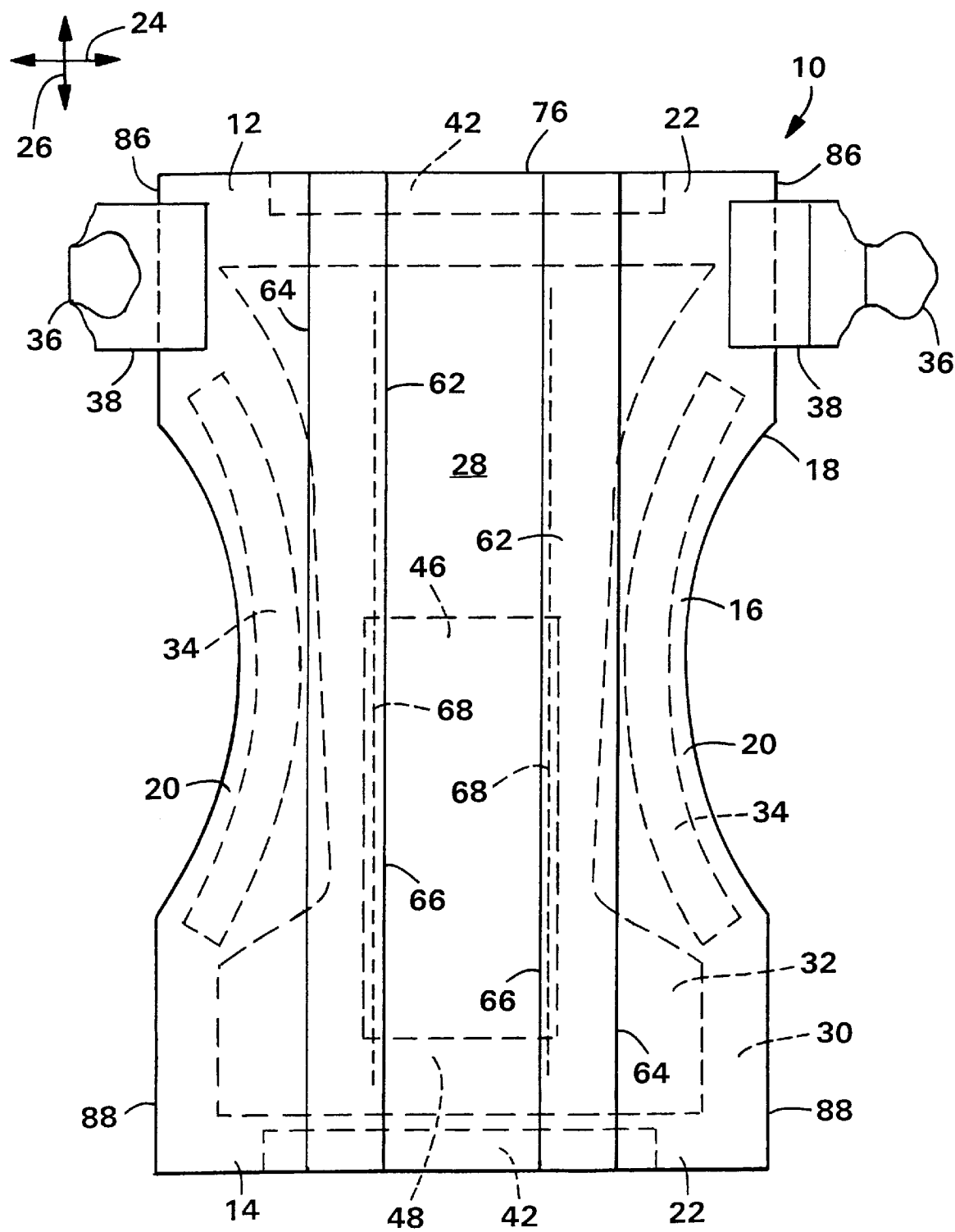
FIG. 1 is a representative, top plan view of a bodyside of a disposable diaper which includes the present invention.
Figure 2:
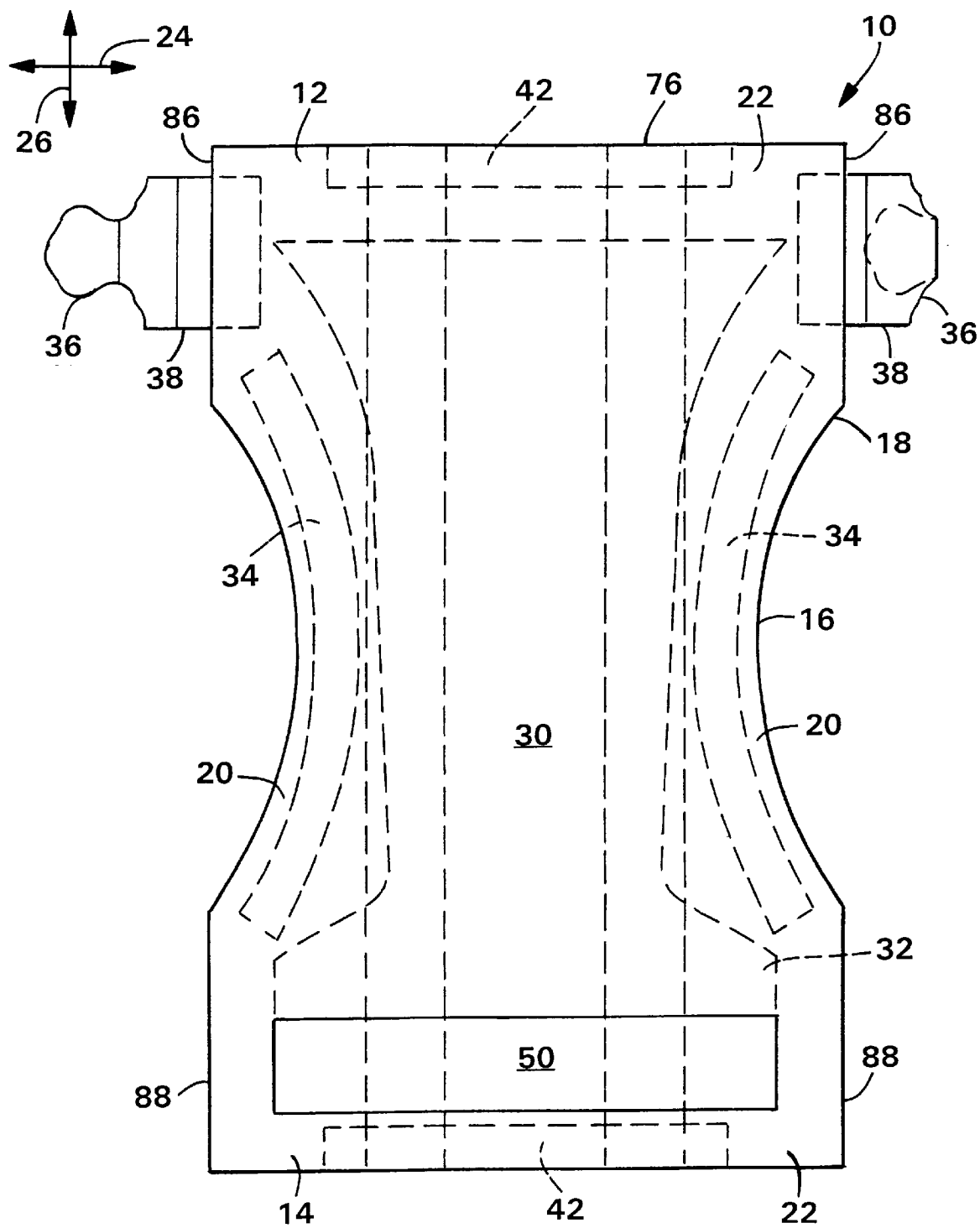
FIG. 2 is a representative, plan view of a outerside of a disposable diaper which includes the present invention.
Figure 3:
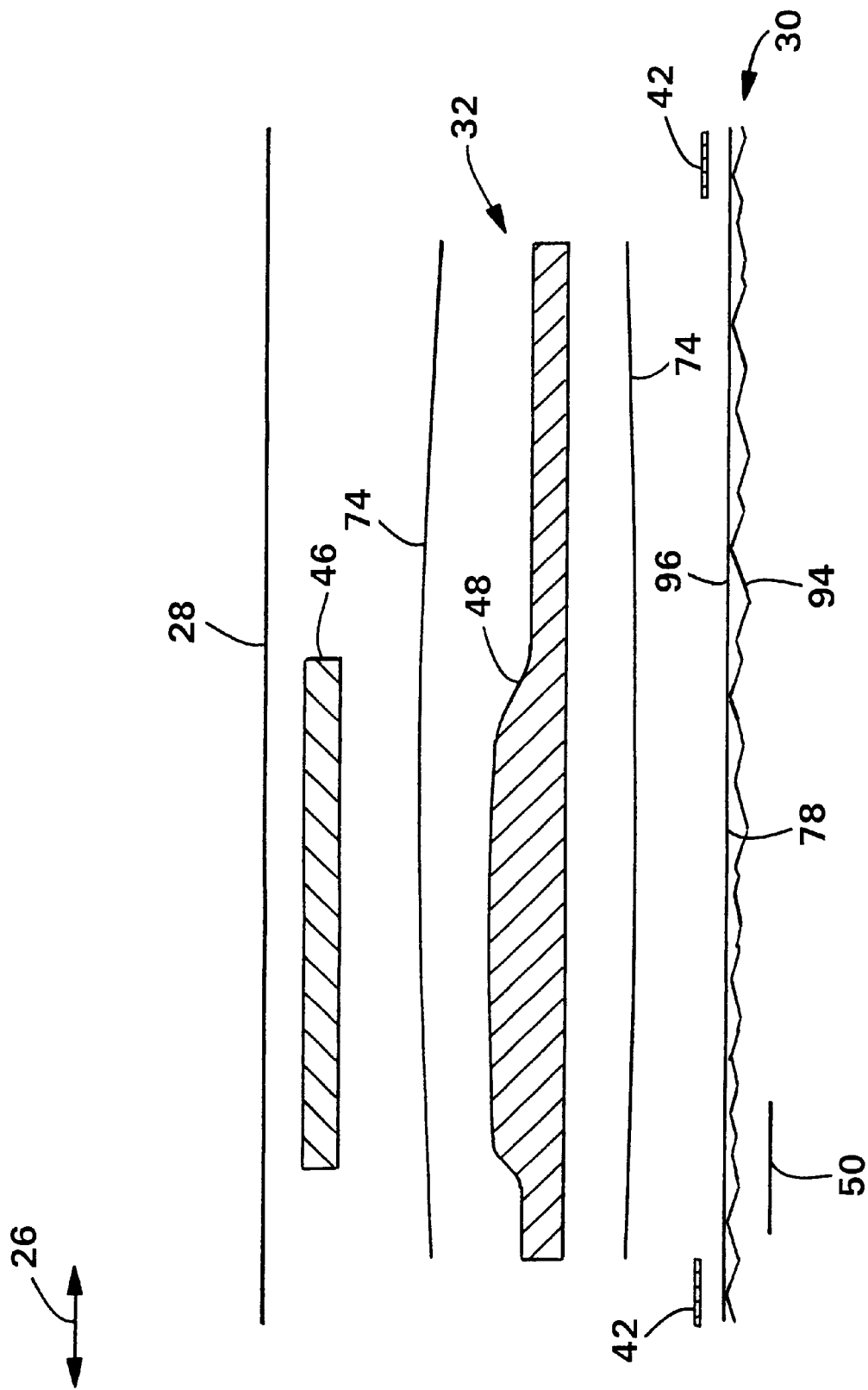
FIG. 3 representatively shows an expanded side view of a configuration the present invention where the outward nonwoven fabric web is directly joined with the air permeable, polymer sheet layer.
Figure 5:
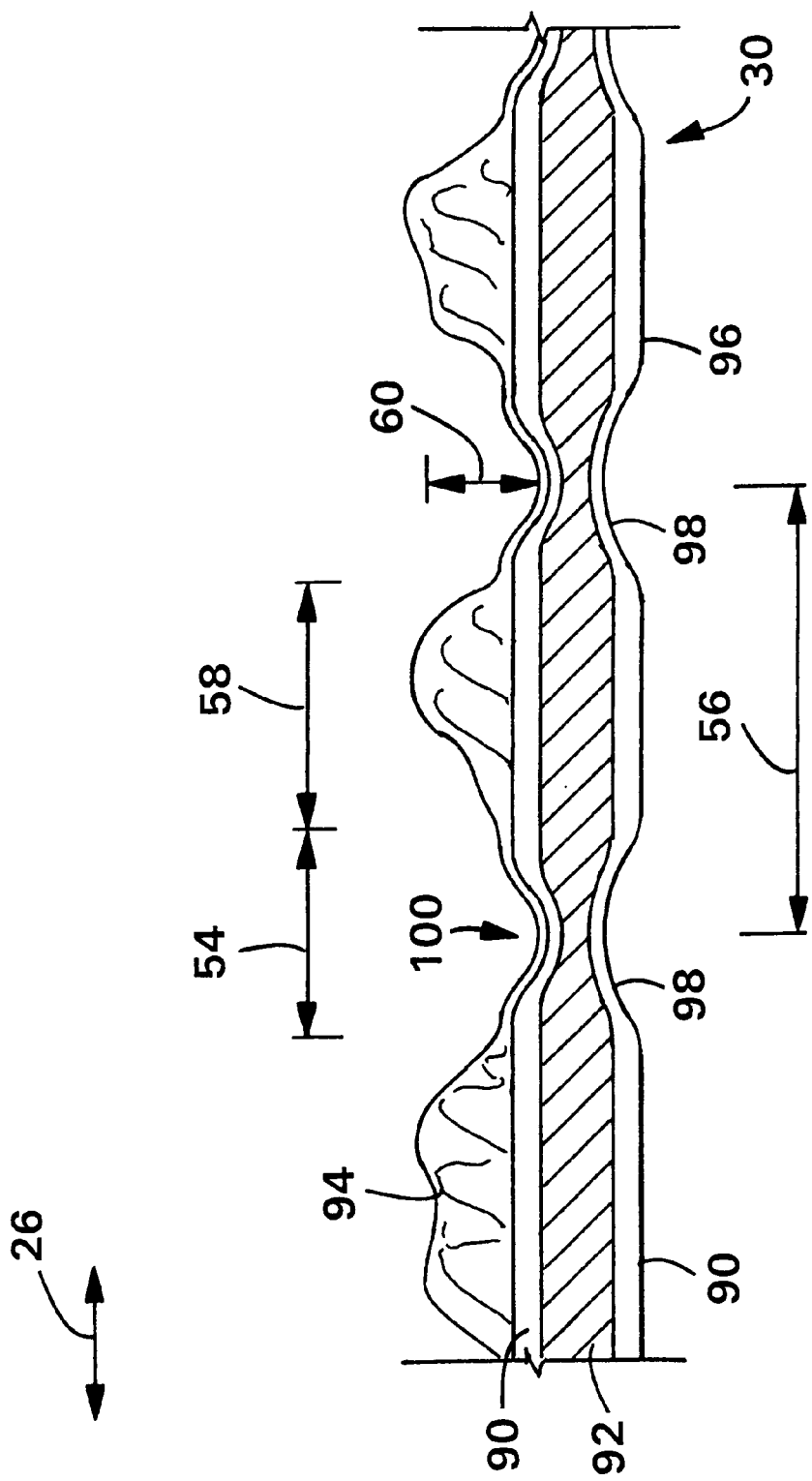
FIG. 5 representatively shows an enlarged cross-sectional view of a backsheet member where the outward nonwoven fabric web is directly joined with the air permeable, polymer sheet layer.

With reference to FIGS. 1, 2 and 3, an article, such as the representatively shown absorbent article of diaper 10, has a length-wise longitudinal direction 26, a transverse lateral direction 24, and a first waistband portion 12 at the back or rear of the diaper. The first waistband portion has an inward, bodyside surface and an outward surface thereof. A second or front waistband portion 14 is positioned longitudinally opposite of the first waistband portion 12 and has an inward, bodyside surface and an outward surface thereof. An intermediate, crotch portion 16 interconnects the first and second waistband portion 12 and 14, respectively. The article includes a flexible and conformable backsheet member 30, a liquid permeable topsheet layer 28, and an absorbent body structure 32. The absorbent body has a retention portion 48, and is sandwiched between the backsheet member 30 and the topsheet layer 28. The backsheet member includes an air permeable, polymer sheet layer 96, and a first, outward nonwoven fibrous web 94 which is attached to or otherwise operatively joined with a major facing surface 78 of the polymer sheet layer 96 at a plurality of individual, spaced apart thermal bonds 98 (FIG. 5). The outward nonwoven web 94 includes a plurality of fibers having substantially unbonded lengths which extend between at least an adjacent pair of the bonds. Desirably, the fibrous unbonded lengths extend substantially continuously, between at least an adjacent pair of the bonds and the substantially unbonded fiber lengths are lofted and desirably arched away from an outward surface of the thermal bonds by distinctive arch heights 60 to provide a desired embossment depth value. More particularly, the unbonded fiber lengths are non-thermally-bonded. In addition, the fibers of the outward nonwoven web can have a selected denier, and the outward nonwoven web 94 can have a selected basis weight.

In desired arrangements, the air permeable polymer sheet layer 96 can have a WVTR value which is at least a minimum of about 500 g/m² per 24 hr, and the unbonded fiber lengths in the outward nonwoven web 94 can have a loftiness, such as provided by the shown arch heights 60, wherein the fiber loftiness and thermal bonding can provide an embossing element depth value of at least a minimum of about 110 μm. In other desired configurations, the fibers of the outward nonwoven web can have a denier of not more than a maximum of about 3 dpf, and the fabric basis weight of the outward nonwoven web can be not more than about 55 g/m².

In further aspects, the outward nonwoven fibrous web 94 may optionally be indirectly joined with the polymer sheet layer 96. For example, the outward nonwoven fibrous web 94 may be directly attached to a first, outward major facing surface 80 of an intermediate nonwoven fibrous web 84 at the plurality of thermal bonds 98, and the polymer sheet layer 96 may be attached to an opposed, second major facing surface 82 of the intermediate nonwoven web 84.

The various aspects (individually and in combination) of the present invention can advantageously help to provide an article having a visually and tactilely distinctive laminate backsheet member. The backsheet member can provide an outer cover having a lofty outward surface, and can be produced at low cost. A distinctive combination of gross embossments and a selected, fibrous nonwoven, outermost laminate layer can provide an aesthetically pleasing outer cover having improved appearance, abrasion resistance and feel, which can more effectively connote desired apparel-like qualities. The selected depths of a gross bonding or embossment pattern and the particular levels of loft in the nonwoven fabric have been found to be important parameters for imparting a desired three-dimensionality in the fibrous surface of an economical, low density, lofty, nonwoven outer cover fabric. Accordingly, the various aspects of the present invention can advantageously provide a distinctive article having a low basis weight backsheet member with improved durability, bulk and softness.

A desired integral garment article of the invention can, for example, be provided by the representatively shown disposable diaper 10. In the diaper, the liquid permeable topsheet layer 28 is operatively joined and assembled with the backsheet layer 30, and the absorbent structure is operably secured and positioned in a laminated arrangement between the backsheet and topsheet layers. A fastening system, such as a system including fasteners 36, is configured to provide a back-to-front fastening in which the back waistband portion 12 can be arranged in an overlapping relation with the front waistband portion 14 to thereby encircle the wearer's body and hold the diaper secure on the wearer during use. Optionally, the fastening system can employ fastener tabs 36 which are configured to provide a front-to-back fastening which arranges and joins the front waistband portion 14 in an overlapping relation with the back waistband portions 12 to thereby encircle the wearer's body during use.

As representatively shown, the front waistband section 14 of the diaper 10 has a laterally opposed, front pair of side edge regions 88, and the rear waistband section 12 has a laterally opposed, rear pair of side edge regions 86. The intermediate section 16 interconnects the front and rear waistband section and provides a diaper crotch region which is typically positioned between the legs of the wearer. The article has an appointed fastener landing member 50 which is disposed on the outward surface of the article. In the example shown in FIG. 2, for example, the landing member 50 is disposed on the outward surface of the backsheet layer 30. The liquid permeable topsheet layer 28 is superposed in facing relation with the backsheet layer 30, and the absorbent body 32 is operably connected and affixed between the backsheet layer 30 and topsheet layer 28. In desired arrangements, the topsheet layer 28 and the absorbent body 32 can be constructed to be substantially nonelastomeric and can be operatively attached to the backsheet member 30 to substantially restrain excessive stretching of the backsheet member.

FIGS. 1 and 2 show typical plan views of the representative disposable diaper 10 in its generally flat-out, uncontracted state (i.e., with substantially all elastic induced gathering and contraction removed), and show the bodyside surface of the diaper, which is intended to contact the wearer, facing the viewer. The outer edges of the diaper define a periphery 18 with longitudinally extending side edge margins 20 and laterally extending end edge margins 22. The side edges define leg openings for the diaper, and optionally, are curvilinear and contoured. The end edges are shown as straight, but optionally, may be curvilinear.

With regard to the designated surfaces of the article and components, the various inward surfaces are configured to face toward the body of the wearer when the article is placed about the wearer. The various outward surfaces are configured to face away from the wearer's body when the article is placed about the wearer.

The diaper 10 typically includes a porous, liquid permeable topsheet 28; a substantially liquid impermeable backsheet 30; an absorbent structure 32 positioned and connected between the topsheet and backsheet; a surge management portion 46 located adjacent the absorbent structure; and a system of elastomeric gathering members, such as a system including leg elastics 34 and waist elastics 42. The surge management portion is positioned in a liquid communication with a retention portion 48 of the absorbent structure, and the topsheet 28, backsheet 30, absorbent structure 32, surge management portion 46 and elastic members 34 and 42 may be assembled together into a variety of well-known diaper configurations. The diaper can additionally include a system of containment flaps 62, and a system of side panel or ear region members 38, which may be elasticized or otherwise rendered elastomeric.

Examples of articles which include elasticized side panels and selectively configured fastener tabs are described in U.S. patent application Ser. No. 168,615 of T. Roessler et al., entitled DYNAMIC FITTING DIAPER, and filed Dec. 16, 1993 (attorney docket No. 10,961). Various techniques for forming the desired fastening systems are described in U.S. Pat. No. 5,399,219 of T. Roessler et al., entitled METHOD FOR MAKING A FASTENING SYSTEM FOR A DYNAMIC FITTING DIAPER and issued Mar. 21, 1995 (attorney docket No. 11,186); in U.S. patent application Ser. No. 286,086 of D. Fries, entitled A PROCESS FOR ASSEMBLING ELASTICIZED EAR PORTIONS and filed Aug. 3, 1994 (attorney docket No. 11,169) which issued as U.S. Pat. No. 5,540,796; and in U.S. patent application Ser. No. 08/415,383 of D. Fries, entitled AN ASSEMBLY PROCESS FOR A LAMINATED TAPE and filed Apr. 3, 1995 (attorney docket No. 11,950) which issued as U.S. Pat. No. 5,595,618. The disclosures of the above-described documents are incorporated herein by reference in a manner that is consistent (not in conflict) herewith.

Diaper 10 generally defines the longitudinally extending length direction 26 and the laterally extending width direction 24, as representatively shown in FIG. 1. The diaper may have any desired shape, such as rectangular, I-shaped, a generally hourglass shape, or a T-shape. With the T-shape, the crossbar of the "T" may comprise the front waistband portion of the diaper, or may alternatively comprise the rear waistband portion of the diaper.

The topsheet 28 and backsheet 30 may be generally coextensive, and may have length and width dimensions which are generally larger than and extend beyond the corresponding dimensions of the absorbent structure 32 to provide for the corresponding side margins 20 and end margins 22. Optionally, the topsheet and backsheet layers may not be coextensive. The topsheet 28 is operatively associated with and superimposed on backsheet 30, thereby defining the periphery of the diaper. The waistband regions comprise those portions of the diaper, which when worn, wholly or partially cover or encircle the waist or mid-lower torso of the wearer. The intermediate, crotch region 16 lies between and interconnects the waistband regions 14 and 12, and comprises that portion of the diaper which, when worn, is positioned between the legs of the wearer and covers the lower torso of the wearer. Thus, the intermediate crotch region 16 is an area where repeated liquid surges typically occur in the diaper or other disposable absorbent article.

Backsheet 30 can typically be located along an outer-side surface of the absorbent body 32 and may be composed of a liquid permeable material, but desirably comprises a material which is configured to be substantially impermeable to liquids. For example, a typical backsheet can be manufactured from a thin plastic film, or other flexible, substantially liquid-impermeable material. As used in the present specification, the term "flexible" refers to materials which are compliant and which will readily conform to the general shape and contours of the wearer's body. Backsheet 30 prevents the exudates contained in absorbent body 32 from wetting articles, such as bedsheets and overgarments, which contact diaper 10. In particular embodiments of the invention, backsheet 30 can include a film, such as a polyethylene film, having a thickness of from about 0.012 millimeters (0.5 mil) to about 0.051 millimeters (2.0 mils). For example, the backsheet film can have a thickness of about 1.25 mil.

Alternative constructions of the backsheet may comprise a woven or non-woven fibrous web layer which has been totally or partially constructed or treated to impart the desired levels of liquid impermeability to selected regions that are adjacent or proximate the absorbent body. For example, the backsheet may include a gas-permeable, non-woven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type forms the outercover of a HUGGIES® ULTRATRIM diaper, which is commercially available from Kimberly-Clark Corporation. The backsheet 30 typically provides the outer cover of the article. Optionally, however, the article may include a separate outer cover component member which is additional to the backsheet. Backsheet 30 may include a micro-porous, "breathable" material which permits gases, such as water vapor, to escape from the absorbent body 32 while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In the various configurations of the invention, where a component, such as the backsheet 30 or the containment flaps 62 are configured to be permeable to gas while having a resistance and limited permeability to aqueous liquid, the liquid resistant component can have a construction which is capable of supporting a hydrohead of at least about 45 cm of water substantially without leakage therethrough. A suitable technique for determining the resistance of a material to liquid penetration is Federal Test Method Standard FTMS 191 Method 5514, dated Dec. 31. 1968.

Accordingly, the backsheet member 30 is sufficiently impermeable to liquid and semi-liquid materials to substantially prevent the undesired leakage of waste materials, such as urine and feces. For example, the backsheet member can desirably support a hydrohead of at least about 45 centimeters (cm) substantially without leakage. The backsheet member 30 can alternatively support a hydrohead of at least about 55 cm, and optionally, can support a hydrohead of at least about 60 cm, or more, to provide improved benefits.

The size of the backsheet 30 is typically determined by the size of absorbent body 32 and the particular diaper design selected. Backsheet 30, for example, may have a generally T-shape, a generally I-shape or a modified hourglass shape, and may extend beyond the terminal edges of absorbent body 32 by a selected distance, such as a distance within the range of about 1.3 centimeters to 2.5 centimeters (about 0.5 to 1.0 inch), to provide at least a portion of the side and end margins.

The topsheet 28 presents a body-facing surface which is compliant, soft-feeling, and non-irritating to the wearer's skin. Further, the topsheet 28 can be less hydrophilic than absorbent body 32, and is sufficiently porous to be liquid permeable, permitting liquid to readily penetrate through its thickness to reach the absorbent body. A suitable topsheet layer 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 28 is typically employed to help isolate the wearer's skin from liquids held in absorbent body 32.

Various woven and nonwoven fabrics can be used for topsheet 28. For example, the topsheet may be composed of a meltblown or spunbonded web of the desired fibers, and may also be a bonded-carded-web. The various fabrics can be composed of natural fibers, synthetic fibers or combinations thereof.

For the purposes of the present description, the term "nonwoven web" means a web of fibrous material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

The topsheet 28 and backsheet 30 are connected or otherwise associated together in an operable manner. As used herein, the term "associated" encompasses configurations in which topsheet 28 is directly joined to backsheet 30 by affixing topsheet 28 directly to backsheet 30, and configurations wherein topsheet 28 is indirectly joined to backsheet 30 by affixing topsheet 28 to intermediate members which in turn are affixed to backsheet 30. Topsheet 28 and backsheet 30 can, for example, be joined to each other in at least a portion of the diaper periphery by attachment mechanisms (not shown) such as adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or an array of separate lines, swirls or spots of construction bonds may be used to affix the topsheet 28 to the backsheet 30. It should be readily appreciated that the above-described attachment mechanisms may also be employed to suitably interconnect, assemble and/or affix together the various other component parts of the articles which are described herein.

The absorbent body 32 provides an absorbent structure which can include a retention portion 48, such as the shown absorbent pad composed of selected hydrophilic fibers and high-absorbency particles, for holding and storing absorbed liquids and other waste materials. The absorbent body is positioned and sandwiched between the topsheet 28 and backsheet 30 to form the diaper 10. The absorbent body has a construction which is generally compressible, conformable, non-irritating to the wearer's skin, and capable of absorbing and retaining body exudates. It should be understood that, for purposes of this invention, the absorbent body structure may comprise a single, integral piece of material, or alternatively, may comprise a plurality of individual separate pieces of material which are operably assembled together.

Various types of wettable, hydrophilic fibrous material can be used to form the component parts of absorbent body 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with such system, fibers having contact angles less than 90° are designated "wettable", while fibers having contact angles greater than 90° are designated "nonwettable".

The absorbent body structure 32 can comprise a matrix of hydrophilic fibers, such as a web of cellulosic fluff, mixed with particles of high-absorbency material. In particular arrangements, absorbent body 32 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823 issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel however", has commonly been used to also refer to both the wetted and unwetted forms of the material.

As mentioned previously, the high-absorbency material used in absorbent body 32 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 32. Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and alternatively is within the range of about 550–750 gsm to provide desired performance.

To improve the containment of the high-absorbency material, absorbent body structure 32 can include an overwrap, such as wrap sheet 74, which is placed immediately adjacent and around absorbent body 32 and may be bonded to the absorbent structure and to the various other components of the article. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrapping which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 74, or at least the bodyside layer of the wrap sheet, may comprise a meltblown web composed of meltblown fibers, such as meltblown polypropylene fibers. Another example of absorbent wrap 74 may comprise a low porosity cellulosic web, such as a tissue composed of an approximately 50/50 blend of hardwood/softwood fibers.

The absorbent wrap 74 may comprise a multi-element wrapsheet which includes a separate bodyside wrap layer and a separate outerside wrap layer, each of which extends past all or some of the peripheral edges of absorbent body 32. Such a configuration of the wrap sheet can, for example, facilitate the formation of a substantially complete sealing and closure around the peripheral edges of absorbent body 32. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 74 can extend at least about ½inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 74 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Diaper 10 can also include a surge management layer 46 which helps to decelerate and diffuse surges of liquid that may be introduced into the absorbent body of the article. In the illustrated embodiment, for example, surge layer 46 can be located on an inwardly facing body side surface of topsheet layer 28. Alternatively, surge layer 46 may be located adjacent to an outer side surface of topsheet 28. Accordingly, the surge layer would then be interposed between topsheet 28 and absorbent body 32. Examples of suitable surge management layers 46 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 (attorney docket No. 11,256) which issued as U.S. Pat. No. 5,486,166; and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 (attorney docket No. 11,387) which issued as U.S. Pat. No. 5,490,846; the entire disclosures of which are hereby incorporated by reference in a manner that is consistent herewith.

Figure 6:
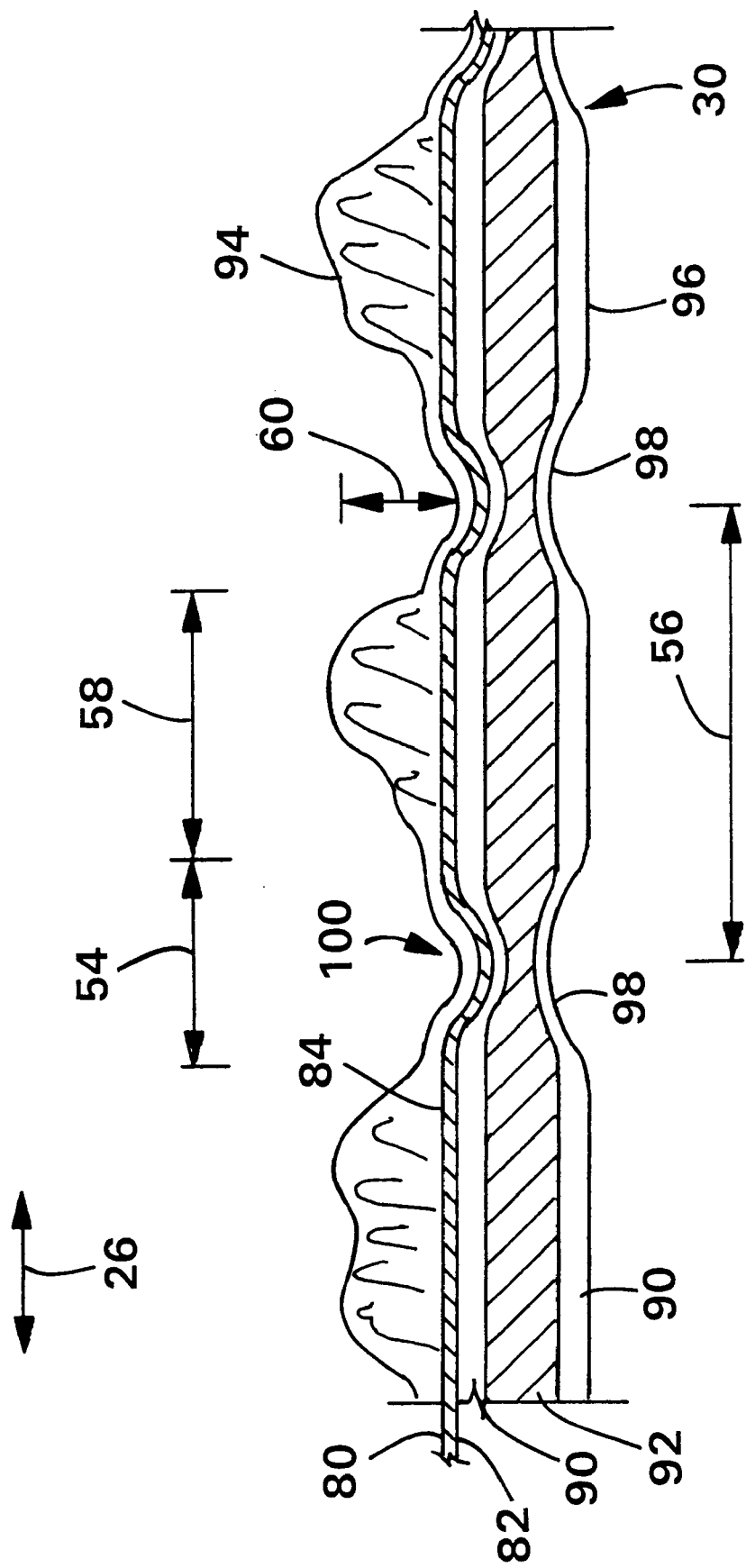
FIG. 6 representatively shows an enlarged cross-sectional view of a backsheet member where the outward nonwoven web is indirectly joined with the air permeable, polymer sheet layer by employing an intermediate nonwoven fabric web.

With reference to FIGS. 5 and 6, further aspects of the invention can provide an article wherein the backsheet member 30 includes a laminate material having at least an outward fibrous nonwoven web 94 which is attached to or is otherwise operatively joined with the polymer sheet layer 96. The nonwoven fabric 94 may be directly or indirectly attached with the polymer sheet layer, and may, for example, be a spunbonded nonwoven, such as a polypropylene spunbond.

In the various aspects and configurations of the invention, the fibers of the outward nonwoven web 94 may have a denier size of not more than a maximum of about 3 denier per filament (dpf). In particular aspects, the fiber denier can be not less than about 1 dpf, and desirably, the fiber denier can be approximately 1.5 dpf to provide improved softness and appearance.

With the configuration representatively shown in FIGS. 3 and 5, the first, outward nonwoven fibrous web 94 can be directly attached to the polymer sheet layer 96 at the plurality of thermal bonds. Accordingly, the thermal bonds 98 can provide a fused attachment directly onto the immediately adjacent polymer sheet layer 96.

Figure 4:
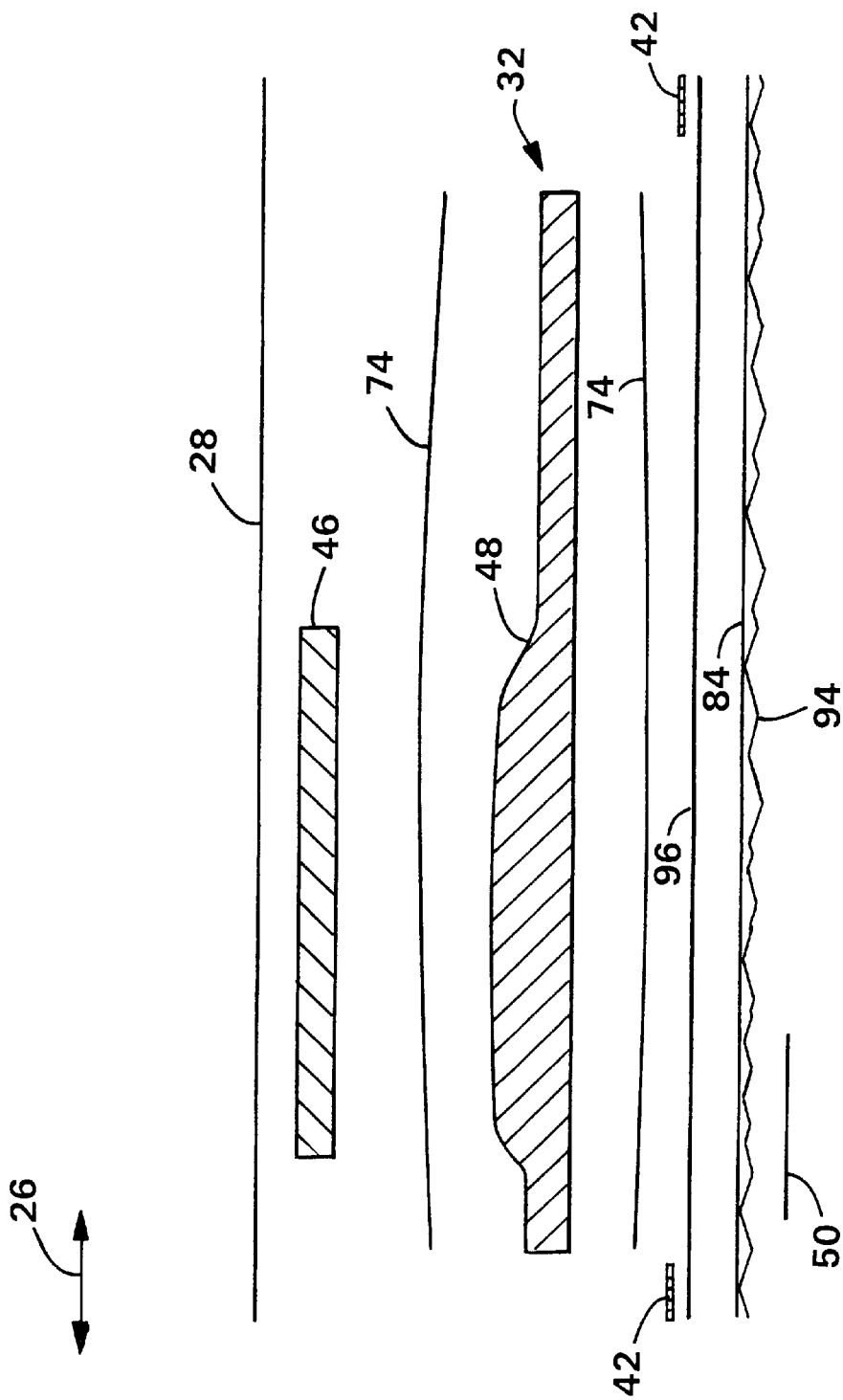
FIG. 4 representatively shows an expanded side view of a configuration the present invention where the outward nonwoven web is indirectly joined with the air permeable, polymer sheet layer by employing an intermediate nonwoven fabric web.

In an alternative aspect of the invention, the outward nonwoven fibrous web 94 can be indirectly attached to the polymer sheet layer 96 at the selected bonding pattern provided by the plurality of thermal bonds. With reference to FIGS. 4 and 6, for example, the outward nonwoven web 94 can be directly attached to an intermediately adjacent, nonwoven fibrous web 84 which has a first major facing surface 80 and a second major facing surface 82. In the illustrated arrangement, the outward nonwoven fibrous web 94 can be directly attached to the first major facing surface 80 of the second, intermediate nonwoven fibrous web 84 at the plurality of thermal bonds 98. The polymer film layer 96 is then attached to the opposite, second major facing surface 82 of the intermediate nonwoven web 84. The attachment may be by any suitable mechanism, such as adhesive bonding, cohesive bonding, sonic bonding, fusion bonding, stapling, pinning or the like, as well as combinations thereof.

In the configuration where the outward nonwoven fibrous web 94 is directly attached to the polymer sheet layer 96, the outward nonwoven fibrous web can have a basis weight which is not less than a minimum of about 6.8 g/m² (about 0.2 oz/yd²). Alternatively, the basis weight is not less than about 10.2 g/m² (about 0.3 oz/yd²) and optionally, is not less than about 13.6 g/m² (about 0.4 oz/yd²). In other aspects, the fabric can have a basis weight of not more than a maximum of about 55 g/m². Alternatively, the basis weight can be not more than about 51 g/m² (about 1.5 oz/yd²), and optionally, can be not more than about 41 g/m² (about 1.2 oz/yd²). In still other aspects, the basis weight can be about 27 g/m² (about 0.8 oz/yd²) to provide improved benefits.

In the configuration of the backsheet member 30 which includes the intermediate nonwoven fabric 84, the basis weight of the outward nonwoven fibrous web 94 can be at least about 4.5 g/m². Alternatively the basis weight can be at least about 8.5 g/m², and optionally can be at least about 11 g/m². In other aspects, the basis weight can be not more than about 20.5 g/m². Alternatively, the basis weight can be not more than about 16.5, and optionally can be not more about 15 g/m² to provide improved benefits.

In addition, the basis weight of the second intermediate nonwoven fabric 84 can be at least about 4.5 g/m². Alternatively the basis weight can be at least about 8.5 g/m², and optionally can be at least about 11 g/m². In other aspects, the basis weight can be not more than about 20.5 g/m². Alternatively, the basis weight can be not more than about 16.5, and optionally can be not more about 15 g/m² to provide desired benefits.

In desired arrangements, the intermediate nonwoven fibrous web 84 can have a basis weight of about 13.6 g/m². In addition, the basis weight of the outward nonwoven fibrous web 94 can be about 13.6 g/m² to provide further improvements.

In the various aspects of the invention, the incorporated fibrous web, such as the outward nonwoven fabric 94, can have a Frasier Porosity value of not more than a maximum value of about 550 cubic feet of air per square foot of web area per minute (about 550 ft³/ft²/min. In other aspects, the Frasier Porosity value can be not less than a minimum value of about 330 ft³/ft²/min. In a desired arrangement, the Frasier Porosity value can be about 470 ft³/ft²/min to provide further improved performance. A suitable procedure for determining the Frasier Porosity values is ASTM D737: "Air Permeability of Textile Fabric".

The Frasier porosity can provide a corresponding indication of the uniformity of the formation of the spunbond web. With the Frasier porosity values that have been indicated, the formation of the fibrous web yields a more uniform bond pattern definition across the web. Without good web formation, the bonding pattern definition can be good in some place and worse in others.

In further aspects of the invention, the incorporated fibrous web, such as the outward nonwoven fabric 94, can have a MD (machine-direction) tensile strength of not less than about 12 pounds-force per inch of web width (about 12 lb/in). In other aspects, the fibrous web can have a MD tensile strength of not more than about 25 lb/in. Desired arrangements can have a MD tensile strength of about 18.8 lb/in to provide improved performance.

The MD tensile strength can serve as an indicator of a fine denier spunbond. For a given basis weight of the web, the finer the denier, the stronger the tensile strength of the web material. The MD tensile strength can be determined in accordance with ASTM D1117-6: "Breaking Load and Elongation of Fabrics".

For the purposes of the present description, the machine-direction of the material is the lengthwise direction along which the web is transported and moved through the apparatus and process for forming and manufacturing the web. In the illustrated configurations of the invention, for example, the machine-direction of the fabric 94 substantially corresponds to the longitudinal direction 26.

In the various configurations of the invention, examples of suitable nonwoven fibrous webs can include webs composed of polypropylene, polyester, nylon, polyethylene as well as combinations thereof. The fibers may have a bicomponent or other multi-component configuration, and the webs may be spunbond fabrics, bonded-carded webs or meltblown fabrics, as well as combinations thereof.

A suitable technique for forming the outward nonwoven fabric 94 with arched fibers is described in European Patent Application EP 0 604 731 of Kimberly-Clark Corporation, entitled STRETCH-PILLOWED, BULKED LAMINATE and published Jun. 7, 1994; the entire disclosure of which is incorporated herein by reference in a manner that is consistent herewith. The polymer sheet layer 96 or the intermediate fabric 84, as appropriate, may be tensioned to generate the desired arched fiber lengths in the outward fabric 94.

With reference to FIGS. 5 and 6, the backsheet member 30 can be bonded and operatively embossed to provide a selected pattern and distribution of embossing elements 100. The bonding elements may regular or irregular in shape, and may have a regular or irregular distribution across the surface area of the backsheet member. The substantially non-thermally-bonded fiber lengths 58 of the extending fibers within the outward nonwoven web 94 are desirably arched or otherwise lofted away from the surface of the thermal bonds 98 by their arched fiber heights 60. The loftiness of the fibers and the selectively applied bonding pattern can be advantageously configured to provide an embossing element depth value which is at least a minimum value of about 160 $\mu$m. Alternatively, the embossing element depth value can be at least about 175 $\mu$m, and optionally, can be at least about 190 $\mu$m to provide desired benefits. In further aspects, the embossing element depth value can be up to about 250 $\mu$m and optionally can be up to about 300 $\mu$m. Additional configurations can have an embossing element depth value of up to a maximum of about 1000 $\mu$m, or more, and a desired configuration has an embossing depth value of about 200 $\mu$m to provide improved benefits.

Conventional techniques can be employed to measure the embossing element depth value of the material provided by the effective depth distances between the surface of the thermal bonds 98 and the tops of substantially unbonded fiber portions which are arched or otherwise lofted above and away from the thermal bonds. In particular, the embossing element depth or the effective pattern depth of the shown thermal bonding on a selected material can be measured by employing a contact stylus profilometer, such as a Model S5 TALYSURF Surface Profilometer manufactured by Rank Taylor Hobson, Ltd., a business having an address at P.O. Box 36, New Star Rd., Leicester LE4 7JQ, England. The stylus used for the measurement is Part Number 112/1836, which includes a nominal 2-micrometer radius, conispherical diamond tip. The stylus position is determined by a laser interferometric transducer traverse unit (Part Number 112/2033) which utilizes a helium-neon laser having a wavelength of 632.8 nm (nanometer), and provides a maximum vertical measurement range of 6 mm with a resolution of 10 nm over that measurement range. The stylus exerts a force of approximately 0.7 mN (milli-Newtons) on the sampled surface. Prior to the data collection, the unit is calibrated using the tungsten carbide ball standard provided by Rank Taylor Hobson, which has a known radius (22.0008 mm) and finish (Part Number 112/1844). The data collection and analysis are performed using FORM TALYSURF version 6.02 software (manufacturer: Rank Taylor Hobson, Ltd).

Figure 6A:
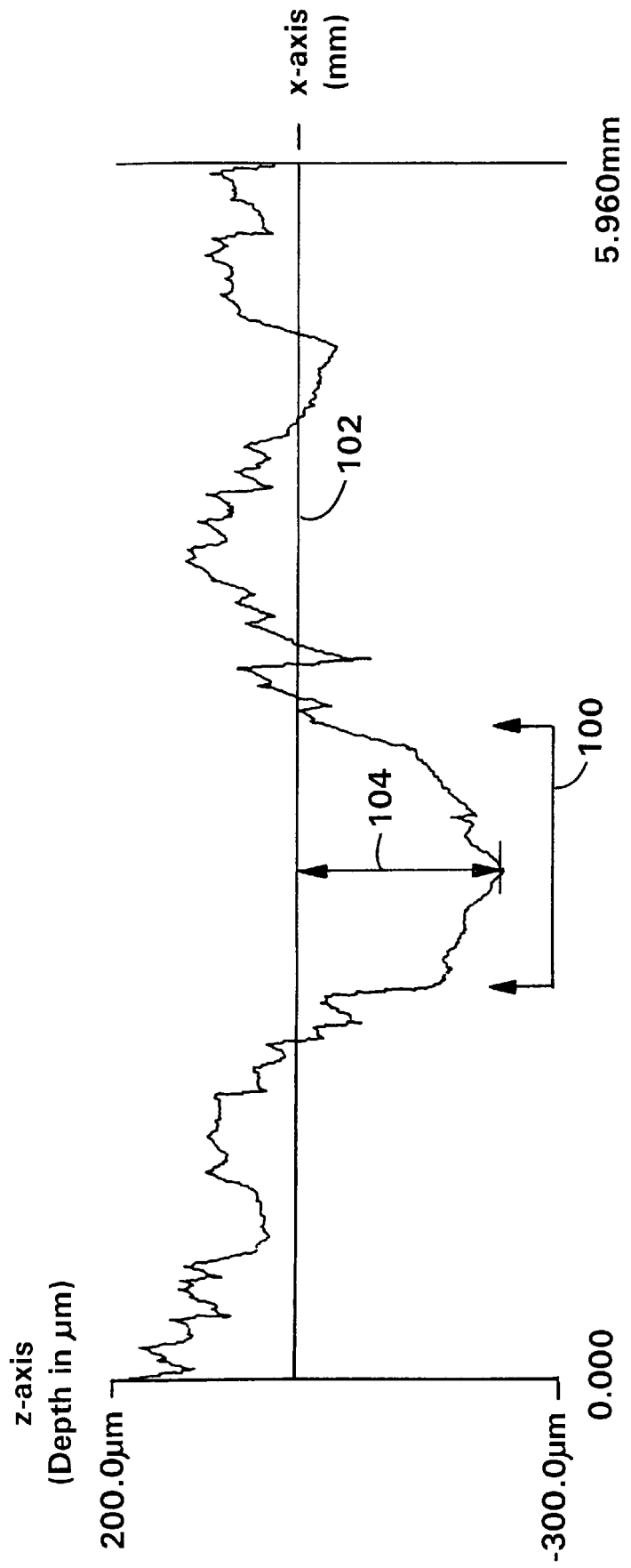
FIG. 6A shows a plot of a representative profilometer trace measuring the depth of an embossing element located on a backsheet member which can be employed with the present invention.

In the test method, a total of five, 6 mm-long traces are made with the stylus tip traversed across different locations of one selected embossment element of the diaper outer cover. For each of the five traces, the stylus tip is drawn across the embossment element along a distance of 6mm, and the trace is oriented substantially perpendicular to the edge of the embossment element at the point where the stylus tip trace path intersects and crosses the embossment element. The trace path is chosen so the stylus tip fully crosses the target embossment element only once and that the midpoint of the trace length occurs approximately at the middle of the width of the embossing element over which the trace passes. The speed of the tip during the traverse is 0.5 mm/sec. The data points for each trace are logged along the trace at each distance interval of 0.25 micrometers. For purposes of analysis, the total number of data points used per trace is 4100, providing a horizontal resolution of 1.46 micrometers. As shown with respect to the representative trace illustrated in FIG. 6A, the depth of embossment 104 is determined as the maximum vertical distance as measured from the linear, least squares best-fit line 102 generated by the software to the lowest point in that portion of the trace corresponding to the embossment element 100. The vertical distance of the depth of embossment is determined for each of the five traces. An arithmetic average of these five vertical distance values is determined, and this arithmetic average is reported as the embossing element depth value. It should be readily appreciated that each set of the five vertical distance values can also be employed to determine a corresponding 1-sigma standard deviation value.

As there is no reference datum line specified in the sample material from which to measure an embossment depth, a straight-line datum reference is established based on all data points contained in each trace. This is the generally accepted procedure for measurement of surfaces which have no independent datum. For each trace, the mean datum reference is automatically determined in the FORM TALYSURF program. The reference datum is graphically displayed in the FORM TALYSURF analysis routine, and is described as the least squares mean line, which is mathematically positioned in the trace such that the deviation of the Y-axis data points about the line is a minimum. The technique of employing the least squares mean fit line is conventionally known and accepted. For example, a statistics reference that describes the derivation is the textbook *STATISTICS*, Second Edition, by Norma Gilbert. Saunders College Publishing, 1981 Chapter 14.

For the purposes of the present invention, the embossing element depth value is determined while the measured material is in its ambient, "slack" or "relaxed" condition, where substantially no external tensions are applied to the material being tested.

In a particular aspect of the invention, a majority of the adjacent thermal bonds 98 are spaced apart along the longitudinal direction 26 by a bond spacing distance 56 (FIGS. 5 and 6) which can be at least about 1 mm. Alternatively the bond spacing distance can be at least about 2 mm, and optionally can be at least about 3 mm to provide desired performance. In other aspects, the longitudinal bond spacing distance can up to about 7 mm. Alternatively, the bond spacing distance can be up to about 7 mm, and optionally can be up to about 10 mm to provide improved benefits. In further arrangements the bond spacing can be up to about 25 mm or even up to about 75 mm, or more, to provide desired performance.

In other aspects of the invention, a majority of the adjacent thermal bonds 98 are spaced apart along the lateral direction 24 by a lateral spacing distance which is at least about 1 mm. Alternatively the bond spacing distance can be at least about 2 mm, and optionally can be at least about 3 mm to provide desired performance. In other aspects, the longitudinal bond spacing distance can up to about 7 mm. Alternatively, the bond spacing distance can be up to about 7 mm, and optionally can be up to about 10 mm to provide improved benefits. In further arrangements the lateral bond spacing can be up to about 75 mm, or more, to provide desired performance.

Figure 7:
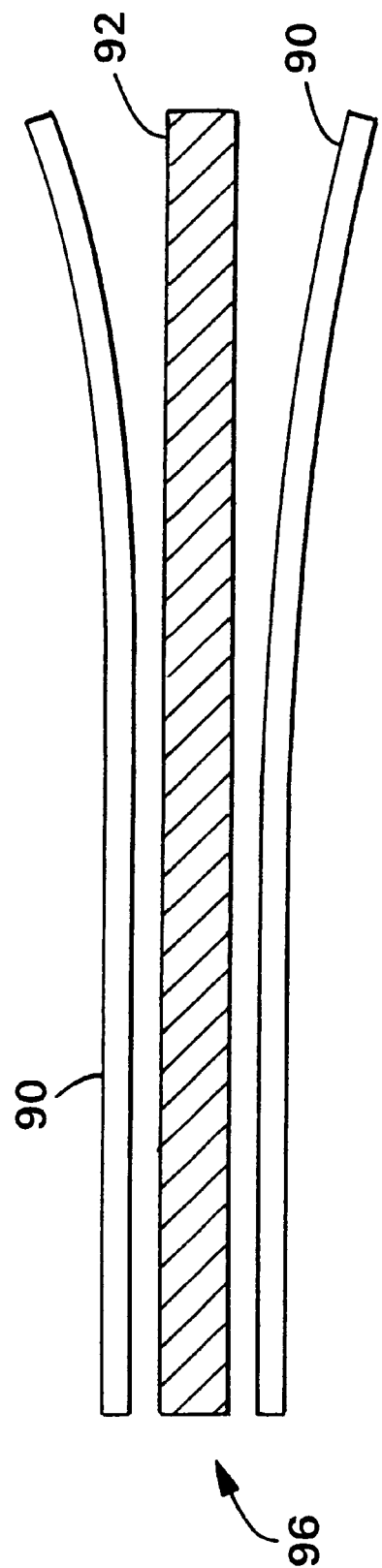
FIG. 7 representatively shows a partially expanded, side view of a laminated polymer sheet layer or film employed with the article of the invention.

With reference to FIGS. 5, 6 and 7, particular aspects of the invention can have the polymer sheet layer 96 configured as a composite sheet having a core layer 92 sandwiched between a pair of skin layers 90 to provide an A-B-A type of film construction. Desirably, the sheet layer is sufficiently gas permeable to be breathable. Suitable techniques and materials for constructing an appropriate polymer sheet layer 96 are described in U.S. patent application Ser. No. 08/882,712 of A. McCormack et al., entitled LOW GAUGE FILMS AND FILM/NONWOVEN LAMINATES and filed Jun. 25,1997 (attorney docket No. 11,436.2), the entire disclosure of which is incorporated herein by reference in a manner that is consistent herewith. Other materials which may be suitable are described in PCT application WO 95/16562 of A. McCormack, filed Jun. 22, 1995 and entitled BREATHABLE CLOTH-LIKE FILM/NONWOVEN COMPOSITE; the entire disclosure of which is incorporated herein by reference in a manner that is consistent herewith.

In another aspect of the invention, the sheet layer 96 can include a linear-low-density-polyethylene (LLDPE) which is desirably present in at least the core layer 92. At least one and desirably both of the skin layers 90 have a composition which is readily compatible with both the nonwoven fabric web 94 and the core layer 92. In particular, the skin layers are configured to readily attach to the nonwoven web 94 upon the application of bonding techniques employing heat and/or pressure. Such techniques can, for example, include thermal bonding, sonic bonding and the like, as well as combinations thereof. Accordingly, the configuration can achieve a sufficiently strong, fused bond between the breathable, stretch-opacified, prominently LLDPE polymer sheet layer 96 and the nonwoven fabric layer 94. The resulting backsheet member 30 can thereby achieve a sufficient level of durability and abrasion resistance desired for an outer cover component.

In a further aspect of the invention, the selected polymer sheet layer 96, particularly the sheet layer composed of the A-B-A LLDPE film, is stretched in a particular manner after it is extruded, formed and cooled. The post-extrusion stretching can produce microscopic holes between the primary polymer material and the calcium carbonate particles contained and distributed within the polymer material, thereby providing the breathability function in the composite backsheet member 30. Additionally, the stretching can produce a stretch-opacifying (e.g."stretch-whitening") of the sheet layer 96. This stretching can render the film opaque or white because of various mechanisms. For example, as the film is stretched, the primary polymer material pulls away from the calcium carbonate particles, thereby producing micropores that refract and scatter incident light. Additionally, the stretching process strains the polymer material past its yield point, thereby imparting a molecular orientation to the primary polymer material. The resulting opacity or whiteness is sufficient to block an observer's view of the wetness that becomes present within the article.

The subsequent gross pattern embossing and fusing operation can employ a concentration of heat and pressure at sufficient amounts which operatively meld the outward nonwoven fabric web 94 with the polymer sheet layer 96 or the intermediate nonwoven fabric 84, as the case may be. The melding helps to affix the outward fabric web 94 to the polymer sheet (or to the intermediate fabric 84) with a strength sufficient to provide suitable durability in the composite backsheet member.

Within the sheet layer 96, the skin layer 90 by virtue of its polymer composition, has a melting point which is intermediate that of the polypropylene fibers and the core layer 92. This can, for example, cause the skin layer to act as a "meltable intermediary" between the fabric web 94 and the core layer 92. In those areas where the opaque sheet layer 96 becomes melted and re-flowed, the sheet layer can regain an amorphous molecular orientation and may acquire a level of translucency. Thus, the gross pattern embossment operation can substantially simultaneously affix together the fabric web 94 and the polymer sheet 96 while also rendering the resulting composite translucent within the area of the fused bonds.

In a representative configuration, the backsheet member 30 can, for example, include a fibrous nonwoven web 94 composed of spunbonded polypropylene fibers, and having a fabric basis weight within the range of about 12–27 g/m$^2$ (about 0.35–0.85 oz/yd$^2$). The nonwoven fibrous web 94 includes about 2 percent titanium dioxide pigment, and is consolidated with a wire-weave, point bonding pattern. The fiber size is desirably about 2 denier per filament (dpf), but could include fiber sizes within the range of about 1–2.5 dpf.

In the representative example of the material for the backsheet member, the cooperating polymer sheet layer 96 can include a core layer 92 composed of about 40% DOW NG3310, about 5.3% DOWLEX 4012, about 50% ECC FILMLINK 2029, and about 2000 ppm (parts per million) of B900. DOW NG 3310 (having a density of about 0.918 g/cc) is linear-low-density-polyethylene (LLDPE) obtained from Dow Chemical USA of Midland, Mich. The DOWLEX 4012 material has a density of about 0.916 g/cc, and is low-density-polyethylene (LDPE) from Dow Chemical USA of Midland, Mich. The FILMLINK 2029 material is a calcium carbonate filler coated with behenic acid, which can be obtained from English China Clay. CIBA B900 is an antioxidant package to provide thermal stability to the polymers during extrusion. The B900 material is a 1:4 ratio of IRGANOX 1076 (a phenolic anti-oxidant) and IRGAFOS 168 (a phosphite stabilizer), and is produced by Ciba Specialty Products. Laminated to each side of the core layer 92 are skin layers 90 which are composed of about 45.1% MONTELL KS357, about 50.4% EXXON 768.36, about 4% SUPERFLOSS, and about 5000 ppm B900. The MONTELL KS357 material is a 30 meltflow rate, random copolymer, ethylene-propylene CATALLOY polymer; and the EXXON 768.36 material is an ethylene-vinyl acetate copolymer, which contains about 28 percent vinyl acetate. The SUPERFLOSS material is diatomaceous earth, produced by Celite Corp, a subsidiary of World Minerals of Lompoc, Calif. The composite sheet 96 can be initially supplied at a basis weight within the range of about 57–65 g/m$^2$, and then operatively stretched about 4.7× to render it breathable. The resulting polymer sheet layer 96 can then have a basis weight which is not less than about 8 g/m$^2$, and optionally is not less than about 17 g/m$^2$. In other aspects, the stretched sheet layer can have a basis weight which is not more than about 35 g/m$^2$, and optionally is not more than about 21 g/m$^2$ to provide desired benefits.

The LLDPE sheet layer 96 can lend itself to producing desired embossments for various reasons. For example, this polymer needs only 50 percent calcium carbonate loading (as opposed a 60 percent for polypropylene polymer) to provide the same target WVTR performance. In addition, the LLDPE polymer has a more amorphous molecular orientation, as compared to polypropylene. The lower calcium carbonate loading and the more amorphous structure can help make the LLDPE sheet layer 96 less liable to split. The lower calcium carbonate loading in LLDPE can help make it more translucent, and the LLDPE sheet layer can be run at lower basis weight. Also, the LLDPE has a lower melting point. As a result, less energy is required in the individual gross pattern embossments to achieve sufficient film and nonwoven melting to produce the desired properties in the bonding areas 98. Thus, the LLDPE sheet layer 96 can better achieve desired levels of aesthetics, durability, and manufacturing speed.

In the various configurations of the invention, the nonwoven web 94 and the polymer sheet layer 96 can be thermally bonded together to form the bonding array of gross pattern embossments. In particular configurations, the array of thermal bonds can be operatively shared between the polymer sheet layer 96 and the nonwoven web 94. The amount of bonding area provided by the shared gross pattern embossment, the basis weight and inherent shred-resistance of the nonwoven web 94, the relatively low extensibility under tension of the nonwoven web, and the inherent strength and stretch properties of the polymer sheet layer 96 (particularly the sheet layer having LLDPE) can all contribute to the desired operability of the present invention. Additionally, the selected configurations of nonwoven web 94 and the material in the core layer 92 of the polymer sheet 96 (such as the core layer configuration containing LLDPE material) can advantageously cooperate to generate translucent gross embossment sites in the backsheet member 30. The resulting laminate can serve as the breathable, moisture impermeable outer cover for a disposable absorbent product, such as a diaper. The inside surface of the outer cover laminate, which is typically provided by the inward facing surface of the sheet layer 96, can operatively receive the application of bonding materials, such as swirl sprays or other patterns of hot melt construction adhesive, to provide the attachments which join the absorbent body 32 to the inward surface of the backsheet member 30, and which join the topsheet 28 to the backsheet member at the perimeter around the absorbent body 32.

The gross pattern embossing, and heat/pressure fusing operation can advantageously provide a combination of different functions. The gross pattern fusing operation can attach and affix together the nonwoven web 94 and the polymer sheet layer 96 to assemble and laminate the backsheet member 30. The gross pattern embossments also provide the overall decorative pattern and a desirable three-dimensionality to the outward surface of the backsheet member outer cover laminate which connotes durable, apparel-like fabric having desired visual and tactile qualities.

Another aspect of the invention can include a composite backsheet member 30 which includes an adhesive bonding and laminating of the nonwoven web 94 to the polymer sheet layer 96. A subsequent thermal processing operation which can then apply heat and pressure to form gross, pattern embossments and a pattern array of thermal bonds 98 in the backsheet member.

In the various aspects of the invention, the resulting composite backsheet member 30 is sufficiently gas-permeable to be deemed breathable. In desired configurations, the backsheet member can provide a WVTR value which is not less than a minimum of about 500 grams per square meter per 24 hours. The WVTR value can be not less than about 1000 grams per square meter per 24 hours, and optionally, can be not less than about 1500 grams per square meter per 24 hours to provide improved humidity control and performance. In further configurations, the backsheet member 30 can have a WVTR of up to about 5000 grams per square meter per 24 hours, or more, to provide further benefits. The WVTR value of a material can be determined in accordance with ASTM Standard E96-80.

Other aspects of the backsheet member 30 can further have an interlaminar peel strength which is at least about 22.5 grams-force per inch of width, and optionally, is at least about 45 grams-force per inch. In other aspects, the backsheet member can have a peel strength which is up to about 75 grams-force per inch, and optionally, is up to the maximum force that can be sustained by the component layers of the backsheet member during a peeling operation. For example, the desired peel strength can be provided between the outward nonwoven web 94 and the polymer sheet 96, between the outward nonwoven web 94 and the intermediate nonwoven web 84, and/or between the intermediate nonwoven web 84 and the polymer sheet 96.

To determine the interlaminar peel strength, a laminate is tested for the amount of tensile force which will pull apart the layers of the laminate. Values for peel strength are obtained using a specified width of fabric, clamp jaw width and a constant rate of extension. For samples having a film side, the film side of the specimen is covered with masking tape, or some other suitable material, in order to prevent the film from ripping apart during the test. The masking tape is on only one side of the laminate and so does not contribute to the peel strength of the sample. This test uses two clamps, each clamp having two jaws with each jaw having a facing in contact with the sample, to hold the material in the same plane, usually vertically, separated by 2 inches to start. The sample size is 4 inches (10.2 cm) wide by as much length as is necessary to delaminate a sufficient amount of sample length. The jaw facing size is 1 inch (2.54 cm) high by at least 4 inches (10.2 cm) wide, and the constant rate of extension is 300 mm/min. The sample is delaminated by hand in an amount sufficient to allow it to be clamped into position. During testing, the clamps move apart at the specified rate of extension to pull apart the laminate. The sample specimen is pulled apart at 180° angle of separation between the two layers, and the peel strength reported is an average of three tests, each of which gather data regarding peak load in grams. The measurement of the desired peeling force data begins when a 16 mm length of the specimen laminate has been pulled apart and delaminated, and the measurement continues until a total of 170 mm of the specimen length has been delaminated. A suitable device for determining the peel strength testing is a SINTECH 2 tester, available from the Sintech Corporation, a business having offices at 1001 Sheldon Dr., Cary, NC 27513; or an INSTRON Model TM, available from the Instron Corporation, a business having offices at 2500 Washington St., Canton, Mass. 02021; or the Thwing-Albert Model INTELLECT II available from the Thwing-Albert Instrument Co., a business having offices at 10960 Dutton Rd., Phila., Penn. 19154. The test may be performed in the cross-direction (CD) 24 of the selected specimen or in the longitudinal direction 26 of the selected specimen from the article.

In further aspects, the backsheet member can exhibit a peak strain value along the longitudinal direction 26 which is at least about 20%, and optionally is at least about 30%. In other aspects, the backsheet member can exhibit a peak strain value along the longitudinal direction 26 which is up to about 40%. Alternatively, the peak strain value can be up to about 60%, and optionally can be up to about 100%, or more, to provide improved performance. The peak strain value can be determined in accordance with standard procedure ASTM D1117-80 and ASTM D5035-90.

Additional aspects of the backsheet member can provide a Taber abrasion value which is at least about 150 cycles, and optionally, is up to about 200 cycles, or more, to provide improved performance. The Taber abrasion value can be determined in accordance with standard procedure FTM-191A, Method 5306. The abrasion measurements are made using a TABER Standard Abrader (Model 503) with rubber wheels #S-32 and a 125 gram counterweight (total load of 125 gram).

Figure 8:
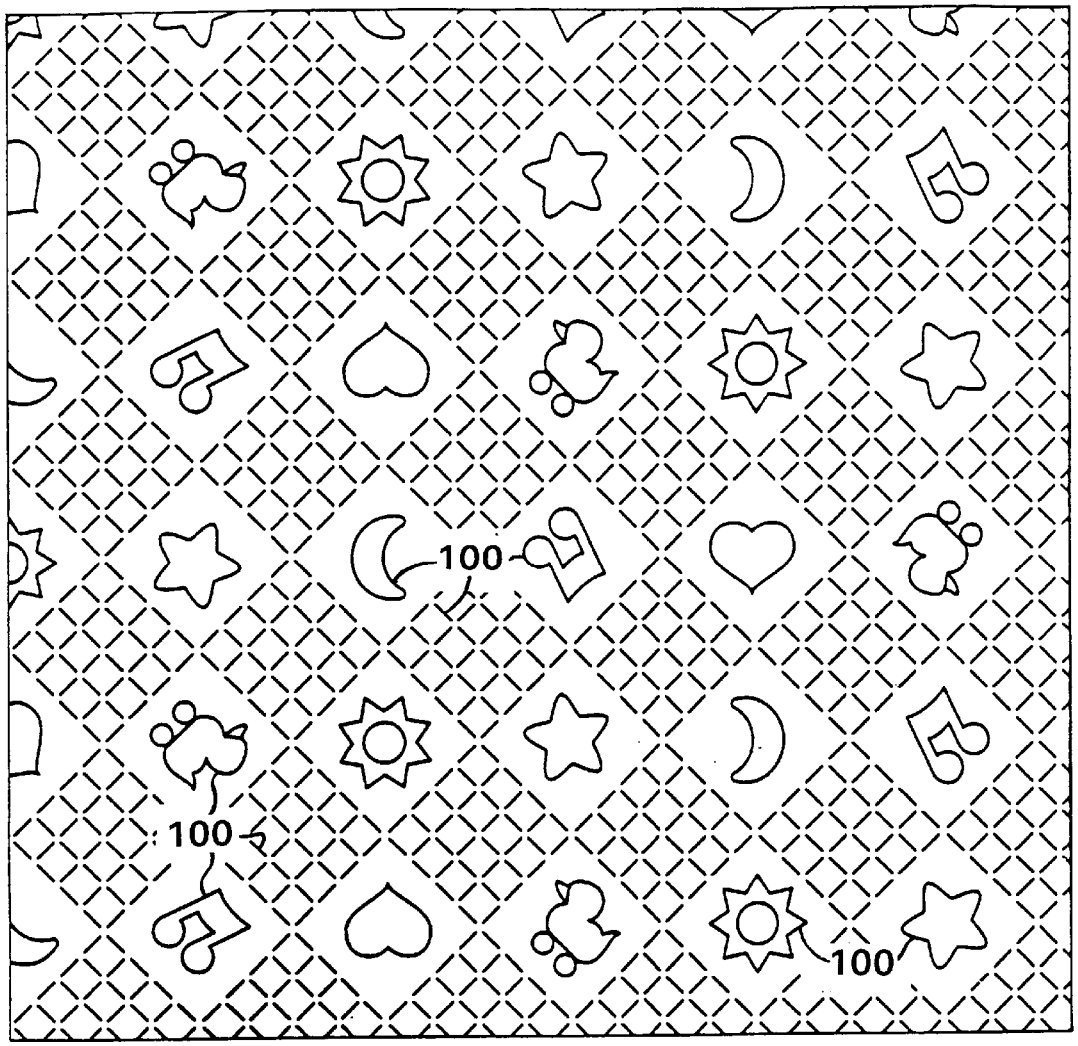
FIG. 8 shows an enlarged, top view of a representative pattern of the thermal bond areas which can be formed across the outer surface area of the backsheet member.

With reference to FIG. 8, a pattern array of thermal bonding areas 98 can be configured in a "Baby Objects" pattern composed of a plurality of contoured bond lines arranged to provide various different shapes, such as stars, moons, hearts and animals, and a plurality of generally linear bond lines arranged to form stripes and other geometric patterns.

Each thermal bond 98 can have a substantially contiguous bonding area of at least of a minimum of about 0.4 mm². The contiguous area of the individual thermal bond is alternatively at least about 0.6 mm², and optionally, is at least about 0.8 mm² to provide improved performance.

In additional aspects of the invention, each thermal bond can have a relatively smaller dimension, such as the shown longitudinal bond length 54 (FIGS. 5 and 6), which is at least a minimum of about 0.01 inches (about 0.254 mm). The bond length 54 is alternatively at least about 0.02 inches (about 0.51 mm), and optionally, is at least about 0.05 inches (about 1.27 mm) to provide improved performance. In further aspects, the relatively smaller bond dimension can be not more than a maximum of about 2 mm. Alternatively, the relatively smaller bond dimension can be not more than about 2.5 mm, and optionally, can be not more than about 3 mm to provide improved benefits. Additionally, each thermal bond area can have a relatively larger dimension which, with respect to any particular point along the selected bond, extends generally perpendicular to the appointed smaller dimension. For example, the larger dimension may be generally linear, may be contoured and non-linear, or may include a combination of straight and curved portions. The larger dimension may extend laterally, longitudinally, or a combination thereof. The larger dimension can be at least a minimum of about 0.0625 inches (about 1.59 mm), and desirably, can be at least about 0.125 inch (about 3.2 mm). Alternatively, the larger dimension bond length can be at least about 1 inch (about 25.4 mm), and optionally, can be at least about 3 inches (about 76.2 mm), or more, to provide further improved benefits.

In the illustrated configuration, each thermal bond is formed by a process which provides sufficient heat and or pressure energy to melt and re-flow the materials of the nonwoven fabric 94 and the polymer sheet layer 96 togenerate the desired thermal bonds and form the bonded composite. The bonding of the polymer layer 96 to the nonwoven fabric layer 94 within the composite laminate material of the backsheet member 30 provides a total thermal bonding area which is at least about 11% of an overall area of the backsheet member 30. The total bonding area is alternatively at least about 14%, and optionally, is at least about 18% of the overall area of the backsheet member. In other aspects, the thermal bonding area can be up to about 25%, and alternatively can be up to about 45%, or more to provide desired benefits.

The elastic members 34 may have any of a multitude of configurations. For example, the width of the individual elastic members 34 may be varied from about 0.25 millimeters (0.01 inch) to about 25 millimeters (1.0 inch) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

In particular embodiments of the invention, the leg elastic members 34 may include a carrier sheet to which are attached agrouped set of elastics composed of a plurality of individual elastic strands. The elastic strands may intersect or be interconnected, or be entirely separated from each other. The carrier sheet may, for example, comprise a 0.002 cm thick polymer film, such as a film of unembossed polypropylene material. The elastic strands can, for example, be composed of LYCRA elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, the leg elastics 34 may begenerally straight or optionally curved. For example, the curved elastics can be inwardly bowed toward the longitudinal centerline of the diaper. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

As representatively shown, the diaper 10 can include a waist elastic 42 positioned in the longitudinal margins of either or both of the front waistband 14 and the rear waistband 12. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent herewith.

With reference to the representative configurations shown in FIGS. 1 and 2, the article can include a system of "ear" regions or ear members 38. In particular arrangements, each ear region or member 38 extends laterally at the opposed, lateral ends of at least one waistband portion of backsheet 30, such as the representatively shown rear waistband portion 12, to provide terminal side sections of the article. In addition, each ear region can substantially span from a laterally extending, terminal waistband edge 76 to approximately the location of its associated and corresponding leg opening section of the diaper. The diaper 10, for example, has a laterally opposed pair of leg openings provided by the curved margins of the ear regions in combination with the correspondingly adjacent, medial sections of the shown pair of longitudinally extending, side edge regions 20 (FIG. 1).

In the various configurations of the invention, the ear regions may be integrally formed with a selected diaper component. For example, ear regions 38 can be integrally formed from the layer of material which provides backsheet layer 30, or may be integrally formed from the material employed to provide topsheet 28. In alternative configurations, the ear regions 38 may be provided by one or more separately provided members that are connected and assembled to the backsheet 30, to the topsheet 28, in between the backsheet and topsheet, or in various fixedly attached combinations of such assemblies. In particular configurations of the invention, each of the ear regions 38 may be formed from a separately provided piece of material which is then suitably assembled and attached to the selected front and/or rear waistband portion of the diaper article. For example, each ear region 38 may be attached to the rear waistband portion of the backsheet 30 along an ear region attachment zone, and can be operably attached to either or both of the backsheet and topsheet components of the article. The inboard, attachment zone region of each ear region can be overlapped and laminated with its corresponding, lateral end edge region of the waistband section of the article. The ear regions extend laterally to form a pair of opposed waist-flap sections of the diaper, and are attached with suitable connecting means, such as adhesive bonding, thermal bonding, ultrasonic bonding, clips, staples, sewing or the like. Desirably, the ear regions extend laterally beyond the terminal side edges of the backsheet layer and topsheet layer at the corresponding, attached waistband section of the article.

The ear regions 38 may be composed of a substantially non-elastomeric material, such as polymer films, woven fabrics, nonwoven fabrics or the like, as well as combinations thereof. In particular aspects of the invention, ear regions 38 may be composed of a substantially elastomeric material, such as a stretch-bonded-laminate (SBL) material, a neck-bonded-laminate (NBL) material, an elastomeric film, an elastomeric foam material, or the like, which is elastomerically stretchable at least along the lateral direction 24. For example, suitable meltblown elastomeric fibrous webs for forming ear regions 38 are described in U.S. Pat. No. 4,663,220 issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP 0 217 032 A2 published on Apr. 8, 1987 which has the listed inventors of J. Taylor et al., the entire disclosure of which is hereby incorporated by reference. Examples of NBL materials are described in U.S. Pat. No. 5,226,992 issued Jul. 13, 1993 to Mormon, the entire disclosure of which is hereby incorporated by reference.

As previously mentioned, various suitable constructions can be employed to attach the ear regions 38 to the selected waistband portions of the article. Particular examples of suitable constructions for securing a pair of elastically stretchable members to the lateral, side portions of an article to extend laterally outward beyond the laterally opposed side regions of the outer cover and liner components of an article can be found in U.S. Pat. No. 4,938,753 issued Jul. 3, 1990 to P. VanGompel et al., the entire disclosure of which is hereby incorporated by reference in a manner that is consistent herewith.

Each of the ear regions 38 extends laterally at a one of the opposed lateral ends of at least one waistband section of the diaper 10. In the shown embodiment, for example, a first pair of ear regions extend laterally at the opposed lateral ends of the back waistband section of the backsheet 30, and a second pair of ear regions extend laterally at the opposed lateral ends of the front waistband section of the backsheet. The illustrated ear regions have a tapered, curved or otherwise contoured shape in which the length of the base region is smaller than the length of its relatively outboard end region. Alternatively, the ear regions may have a substantially rectangular shape or a substantially trapezoidal shape.

Diaper 10 can also include a pair of elasticized containment flaps 62 which extend generally length-wise along the longitudinal direction 26 of the diaper. The containment flaps are typically positioned laterally inboard from leg elastics 34, and substantially symmetrically placed on each side of the lengthwise, longitudinal centerline of the diaper. In the illustrated arrangements, each containment flap 62 has a substantially fixed edge portion 64 and a substantially moveable edge portion 66, and is operably elasticized with at least one elastomeric member 68 to help each containment flap to closely contact and conform to the contours of the wearer's body. Examples of suitable containment flap constructions are described in U.S. Pat. No. 4,704,116 issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, may be permeable to only gas or may be permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT (attorney docket No. 11,375), now U.S. Pat. No. 5,562,650, the disclosure of which is hereby incorporated by reference in a manner that is consistent herewith.

In optional, alternative configurations of the invention, diaper 10 may include internal, elasticized, containment waist flaps, such as those described in U.S. Pat. No. 4,753,646 issued Jun. 28, 1988, to K. Enloe, and in U.S. patent application Ser. No. 560,525 of D. Laux et al. entitled AN ABSORBENT ARTICLE WITH IMPROVED ELASTIC MARGINS AND CONTAINMENT SYSTEM and filed Dec. 18,1995 (attorney docket No. 11,091), the entire disclosures of which are hereby incorporated by reference in a manner that is consistent herewith. Similar to the construction of the containment flaps, the containment waist flaps may be composed of a wettable or non-wettable material, as desired. The waist flap material may be substantially liquid-impermeable, permeable to only gas, or permeable to both gas and liquid.

To provide a desired refastenable fastening system, diaper 10 can include one or more appointed landing member regions, such as a first, primary landing member 50 (e.g. FIGS. 2 and 3), which can provide an operable target area for receiving a releasable and re-attachable securement of the fastener tabs 36 thereon. In particular embodiments of the invention, the landing member patch can be positioned on the front waistband portion 14 of the diaper and is located on the outward surface of the backsheet layer 30. Alternatively, the landing member patch can be positioned on an appointed inward surface of the diaper, such as the bodyside surface of the topsheet layer 28. The fastening mechanism between the landing member and the fastener tabs 36 may be adhesive, cohesive, mechanical or combinations thereof. In the context of the present invention, a mechanical fastening system is a system which includes cooperating components which mechanically inter-engage to provide a desired securement.

A configuration which employs a releasable, interengaging mechanical fastening system can, for example, locate a first element of the mechanical fastener on the landing member 50 and a second, cooperating element of the mechanical fastener on the fastener tab 36. For example, with a hook-and-loop fastener, the hook material can be operably connected and affixed to the fastener tabs 36 and the loop material can be operably connected and affixed to the landing member 50. Alternatively, the loop material can be operably connected to the fastener tabs 36 and the hook material can be operably connected to the landing member 50.

In the various embodiments of the invention, a separately provided tape fastener tab 36 can be located at either or both of lateral end regions 86 and 88 of either or both of the waistbands 14 and 12. The representatively shown embodiment, for example, has one of the fastener tabs 36 located at each of the distal side edges of the rear waistband 12. More particularly, each of the fasteners 36 is assembled and attached to extend from a corresponding, immediately adjacent ear region at one of the opposed lateral ends of the back waistband section 12.

In the various configurations of the invention, the first and/or second fastening component may include an adhesive, a cohesive, a complementary element of an interengaging mechanical fastening system, or the like, as well as combinations thereof. The mechanical fastener components can be provided by mechanical-type fasteners such as hooks, buckles, snaps, buttons and the like, which include cooperating and complementary, mechanically interlocking components. For example, the mechanical fastening system may be a hook-and-loop type of fastening system. Such fastening systems generally comprise a "hook" or hook-like, male component, and a cooperating "loop" or loop-like, female component which engages and releasably interconnects with the hook component. Desirably, the interconnection is selectively releasable and re-attachable. Conventional systems are, for example, available under the VELCRO trademark. The hook element may be provided by a single or multiple hook configuration, such as provided by a mushroom-head type of hook element. The loop element may be provided by a woven fabric, a nonwoven fabric, a knitted fabric, a perforated or apertured layer, and the like, as well as combinations thereof. The many arrangements and variations of such fastener systems have been collectively referred to as hook-and-loop fasteners.

In desired arrangements of the invention, the first fastening component and/or the second fastening component may include a hook type of mechanical fastening element. Accordingly, the corresponding first landing member component and/or second landing member component can include a complementary loop element.

It should also be readily apparent that, in the various configurations of the invention, the relative positions and/or materials of the fastening component and its corresponding landing member component can be transposed. For example, in a hook-and-loop fastening system, the first and/or second fastening component may optionally be composed of a loop element and the first and/or second landing member components may be provided by a hook-type element.

Examples of suitable hook-and-loop fastening systems are described in U.S. Pat. No. 5,019,073 issued May 28, 1991 to T. Roessler et al., the entire disclosure of which is hereby incorporated by reference in a manner that is consistent herewith. Other examples of hook-and-loop fastening systems are described in U.S. patent application Ser. No. 366,080 entitled HIGH-PEEL TAB FASTENER, filed Dec. 28, 1994 by G. Zehner et al. (attorney docket No. 11,571) which issued as U.S. Pat. No. 5,605,735; and U.S. patent application Ser. No. 421,640 entitled MULTI-ATTACHMENT FASTENING SYSTEM, filed Apr. 13, 1995 by P. VanGompel et al.; the entire disclosures of which are hereby incorporated by reference in a manner that is consistent herewith.

Examples of fastening tabs constructed with a carrier layer are described in U.S. patent application Ser. No. 08/603,477 of A. Long et al., entitled MECHANICAL FASTENING SYSTEM WITH GRIP TAB and filed Mar. 6, 1996 (attorney docket No. 12,563), the entire disclosure of which is hereby incorporated by reference in a manner which is consistent herewith.

In a typical configuration of a hook-and-loop fastening system, the hook material member is operably connected to the fastening tab 36, and the loop material is employed to construct at least one cooperating landing member 50. The landing member can, for example, be suitably positioned on the exposed, outward-side surface of the backsheet 30. As previously mentioned, an alternative configuration of the hook-and-loop fastening system may have the loop material secured to the fastener tab 36 and may have the hook material employed to form the landing member 50.

In the various aspects and configurations of the invention, the hook element material can be of the type referred to as micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.033–0.097 cm (about 0.013 to 0.038 inch); and a cap width which is within the range of about 0.025–0.033 cm (about 0.01 to 0.013 inch). The hooks are attached to a base film substrate having a thickness of about 0.0076–0.01 cm (about 0.003–0.004 inch) and a Gurley stiffness of about 15 mgf.

Another suitable micro-hook material is distributed under the designation VELCRO CFM-29 1058, and is available from VELCRO U.S.A., Inc., a business having offices in Manchester, N. H. The micro-hook material can have hooks in the shape of angled hook elements, and can be configured with a hook density of about 264 hooks per square centimeter (about 1700 hooks per square inch); a hook height which is within the range of about 0.030–0.063 cm (about 0.012–0.025 inch); and a hook width which is within the range of about 0.007 to 0.022 cm (about 0.003 to 0.009 inch). The hook elements are coextruded with a base layer substrate having a thickness of about 0.0076–0.008 cm (about 0.003–0.0035 inch), and the member of hook material has a Gurley stiffness of about 12 mgf (about 12 Gurley units).

For the purposes of the present invention, the various stiffness values are determined with respect to a bending moment produced by a force which is directed perpendicular to the plane substantially defined by the length and width of the component being tested. A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N. Y. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

In the various aspects and configurations of the invention, the loop material can be provided by a nonwoven, woven or knit fabric. For example, a suitable loop material fabric can be composed of a 2 bar, warp knit fabric of the type available from Guilford Mills, Inc., Greensborough, N. C. under the trade designation #34285, as well other of knit fabrics. Suitable loop materials are also available from the 3M Company, which has distributed a nylon woven loop under their SCOTCHMATE brand. The 3M Company has also distributed a linerless loop web with adhesive on the backside of the web, and 3M knitted loop tape.

In particular aspects of the invention, the loop material need not be limited to a discrete landing member patch. Instead the loop material can, for example, be provided by a substantially continuous, outer fibrous layer which is integrated to extend over substantially the total exposed surface area of a cloth-like outer cover employed with the diaper 10. The resultant, cloth-like backsheet 30 can thereby provide the loop material for an operative "fasten anywhere" mechanical fastening system.

In the various configurations of the invention, the engagement force between the particular fastening component and its appointed landing member component should be large enough and durable enough to provide an adequate securement of the article on the wearer during use. In desired configurations, the engagement force can provide a peel force value of not less than about 75 grams-force (gmf). Alternatively, the peel force is not less than about 100 gmf, and optionally is not less than about 400 gmf. In particular aspects, the peel force is not more than about 1,200 gmf. Alternatively, the peel force is not more than about 800 gmf, and optionally is not more than about 600 gmf. The engagement force can additionally provide a shear force value of not less than about 1,000 gmf. Alternatively, the shear force is not less than about 2,000 gmf, and optionally, is not less than about 3,000 gmf. In further aspects, the shear force is not more than about 10,000 gmf. Alternatively, the shear force is not more than about 9,000 gmf, and optionally is not more than about 8,000 gmf.

The peel force can be determined in accordance with standard procedure ASTM D5170, approved Sep. 15, 1991 and published November 1991. The shear force value can be determined in accordance with the standard procedure ASTM D-5169, approved Sep. 15, 1991 and published November 1991.

Each of the fastening components and elements in the various constructions of the invention may be operably attached to its supporting substrate by employing any one or more of the attachment mechanisms employed to construct and hold together the various other components of the article of the invention. The fastening elements in the various fastening regions, may be integrally formed, such as by molding, co-extrusion or the like, along with the associated substrate layer. The substrate layer and its associated mechanical fastening elements may be formed from substantially the same polymer material, and there need not be a discrete step of attaching the fastening elements to an initially separate substrate layer. For example, the individual hook elements may be integrally formed simultaneously with a hook base-layer by coextruding the base layer and hook elements from substantially the same polymer material.

It should be readily appreciated that the strength of the attachment or other interconnection between the substrate layer and the attached fastening component should be greater than the peak force required to remove the fastener tab 36 from its releasable securement to the appointed landing member of the article.

EXAMPLES

The following examples are presented to provide a more detailed understanding of the invention. The examples are representative, and are not intended to limit the scope of the invention.

The embossing element depth values for five outercover materials were determined in accordance with the present invention. The measurement data for the five sample materials are summarized in the following TABLE 1.

TABLE 1

| Repetition | Embossing Element Depth Value ($\mu$m) | | | | |
| --- | --- | --- | --- | --- | --- |
| | Code A | Code B | Code C | Code D | Code E |
| 1 | 245.4 | 62.5 | 50.6 | 109.4 | 148.1 |
| 2 | 268.5 | 156.2 | 46.6 | 104.8 | 170.5 |
| 3 | 287.2 | 115.7 | 36.5 | 97.9 | 102.6 |
| 4 | 246.9 | 69.9 | 57.9 | 99.6 | 127.5 |

TABLE 1-continued

| | Embossing Element Depth Value (µm) | | | | |
|---|---|---|---|---|---|
| Repetition | Code A | Code B | Code C | Code D | Code E |
| 5 | 245.6 | 68.6 | 64.5 | 114.1 | 115.3 |
| Arithmetic Average | 258.7 | 94.6 | 51.2 | 105.2 | 132.8 |
| Embossment Pattern Type | Heart | Star | Spunbond Bonds | Star | Star |

Code A was a spunbonded (SB) stretch-thermal laminate (STL) outer cover material composed of two, 0.4 osy (13.6 g/m²) basis weight spunbonded polypropylene fabric layers which were bonded to each other. The two, interconnected spunbonded layers were then bonded to a 0.5 osy (17 g/m²) cast, coextruded polyethylene film. The completed laminate was constructed in accordance with European Patent Application No. EP 0 604 731 A1, and configured in accordance with the present invention.

Code B was an outer cover material obtained from a MOONY DELICATE CARE diaper, which was produced in Japan by UniCharm Corporation, a business with offices in Tokyo, Japan.

Code C was an outer cover material obtained from a SUPERMERRIES diaper, which was produced in Japan by Kao Corporation, a business with offices in Tokyo, Japan.

Code D was an outer cover material obtained from a diaper produced in Korea by Yuhan-Kimberly, a business with offices in Seoul, South Korea.

Code E was an outer cover material obtained from a MOONY POWERSLIM diaper, which was produced in Japan by UniCharm Corporation, a business with offices in Tokyo, Japan.

Consumer preference studies were conducted to assess the improvements afforded by the present invention. The results of the studies are summarized in the following TABLE 2.

TABLE 2

| | Consumer Preference Data (Lower number = Higher Preference) | | Embossing Element Depth |
|---|---|---|---|
| | Test Study - 1 | Test Study - 2 | Value (µm) |
| Code 1 | 325 | | 282 |
| Code 2 | 332 | | 228 |
| Code 3 | | 232 | 220 |
| Code 4 | 509 | 277 | 41 |
| Code 5 | 618 | 349 | 17 |

Each study included 100–150 responses. Participants were shown several diaper codes and were asked to rank the outer covers from the one liked the most to the one liked the least, based on a visual assessment.

Code 1 was a spunbonded (SB) stretch-thermal laminate (STL) outer cover material composed of two plies of a 0.4 osy (13.6 g/m²) spunbonded polypropylene fabric assembled in accordance with EP 0 604 731 A1.

Code 2 was a breathable, stretch-thermal laminate material composed of a 0.8 osy (27.2 g/m²) spunbond fabric and a 23 g/m², A-B-A polypropylene micro-porous film obtained from Edison Plastics, a business having offices in Newport News, Virginia.

Code 3 was a double-embossed, 1.0 osy (34 g/m²) spunbond-meltblown-spunbond (SMS) fabric laminate, which was composed of 9 g/m² copolymer spunbond fibers, 16 g/m² polypropylene meltblown fibers and 9 g/m² copolymer spunbond fibers.

Code 4 was a 0.8 osy (27.2 g/m²) SMS fabric composed of 9.5 g/m² polypropylene spunbond fibers, 8.2 g/m² polypropylene meltblown fibers and 9.5 g/m² polypropylene spunbond fibers.

Code 5 was an outer cover material obtained from a PAMPERS PREMIUM diaper produced by Procter & Gamble Co., a business having offices in Cincinnati, Ohio.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. An absorbent article having a front waistband portion, a back waistband portion and an intermediate portion interconnecting said front and back waistband portions, said article comprising:

a backsheet member;

a liquid permeable topsheet layer; and an absorbent body sandwiched between said topsheet layer and backsheet member;

said backsheet member including;

an air permeable, polymer sheet layer having a WVTR value of at least about 500 g/m² per 24 hr;

an outward nonwoven fibrous web joined with a major facing surface of said polymer sheet layer at a plurality of individual, spaced apart thermal bonds; said outward nonwoven web including a plurality of fibers having substantially unbonded lengths which extend substantially continuously between at least an adjacent pair of said bonds, said substantially unbonded fiber lengths lofted away from an outward surface of said thermal bonds to provide an embossing element depth value of at least about 160 µm, said fibers of said outward nonwoven web having a denier of not more than about 3 dpf, said outward nonwoven web having a basis weight of not more than about 55 g/m².

2. An article as recited in claim 1, wherein said outward nonwoven fibrous web is directly attached to said polymer sheet layer at said plurality of thermal bonds.

3. An article as recited in claim 1, wherein said outward nonwoven fibrous web is indirectly attached to said polymer sheet layer at said plurality of thermal bonds.

4. An article as recited in claim 3, wherein said outward nonwoven fibrous web is directly attached to a first major facing surface of an intermediate nonwoven fibrous web at said plurality of thermal bonds, and said polymer sheet layer is attached to a second major facing surface of said intermediate nonwoven web.

5. An article as recited in claim 4, wherein said fibers provide an embossing element depth value of at least about 175 µm.

6. An article as recited in claim 4, wherein said outward nonwoven fibrous web has a basis weight of about 13.6 g/m².

7. An article as recited in claim 6, wherein intermediate nonwoven fibrous web has a basis weight of about 13.6 g/m².

8. An article as recited in claim 4, wherein thermal bonds provide a bonding area of at least about 11% of a total area of said backsheet member.

9. An article as recited in claim 4, wherein thermal bonds provide a bonding area of up to about 45% of a total area of said backsheet member.

10. An article as recited in claim 4, wherein said polymer sheet layer is a composite laminate composed of a core layer sandwiched between a pair of skin layers; said core layer including a linear-low-density-polyethylene.

11. An article as recited in claim 4, wherein said topsheet layer and said absorbent body are substantially nonelastomeric and are attached to restrain excessive stretching of said backsheet member.

12. An article as recited in claim 4, wherein at least a majority of adjacent thermal bonds are spaced apart by a distance which is at least about 1 mm, and up to about 25 mm.

13. An article as recited in claim 1, wherein said fibers provide an embossing element depth value of at least about 175 μm.

14. An article as recited in claim 1, wherein outward nonwoven fibrous web has a basis weight of about 27 g/m$^2$.

15. An article as recited in claim 1, wherein thermal bonds provide a bonding area of at least about 11% of a total area of said backsheet member.

16. An article as recited in claim 1, wherein thermal bonds provide a bonding area of up to about 45% of a total area of said backsheet member.

17. An article as recited in claim 1, wherein said polymer sheet layer includes an adhesive attachment to said outward nonwoven web.

18. An article as recited in claim 1, wherein said topsheet layer and said absorbent body are substantially nonelastomeric and are attached to restrain excessive stretching of said backsheet member.

19. An article as recited in claim 1, wherein a majority of adjacent thermal bonds are spaced apart by a distance which is at least about 1 mm and up to about 25 mm.

20. An absorbent article having a front waistband portion, a back waistband portion and an intermediate portion interconnecting said front and back waistband portions, said article comprising:

a backsheet member;

a liquid permeable topsheet layer; and an absorbent body sandwiched between said topsheet layer and backsheet member;

said backsheet member including;

an air permeable, polymer sheet layer having a WVTR value of at least about 500 g/m$^2$ per 24 hr, wherein said polymer sheet layer is a composite laminate composed of a core layer sandwiched between a pair of skin layers, with said core layer including a linear-low-density-polyethylene; and an outward nonwoven fibrous web joined with a major facing surface of said polymer sheet layer at a plurality of individual, spaced apart thermal bonds;

said outward nonwoven web including a plurality of fibers having substantially unbonded lengths which extend substantially continuously between at least an adjacent pair of said bonds, said substantially unbonded fiber lengths lofted away from an outward surface of said thermal bonds to provide an embossing element depth value of at least about 160 μm, said fibers of said outward nonwoven web having a denier of not more than about 3 dpf, said outward nonwoven web having a basis weight of not more than about 55 g/m$^2$.

* * * * *